US012662482B2

(12) United States Patent
Liu et al.

(10) Patent No.: US 12,662,482 B2
(45) Date of Patent: Jun. 23, 2026

(54) COMPOUNDS WHICH INHIBIT RNA POLYMERASE

(71) Applicants: The Johns Hopkins University, Baltimore, MD (US); Lieber Institute, Inc., Baltimore, MD (US)

(72) Inventors: Hester Hui Liu, Cockeysville, MD (US); James C. Barrow, Arnold, MD (US); Marikki K. Laiho, Kauniainen (FI); Rajesh Kumar Nv, Baltimore, MD (US); Pablo de Leon, Baltimore, MD (US); Tony Dorado, Baltimore, MD (US); Asma Begum, Baltimore, MD (US); Wenjun Fan, Baltimore, MD (US); Gregory Stachelek, Baltimore, MD (US)

(73) Assignees: The Johns Hopkins University, Baltimore, MD (US); Lieber Institute, Inc., Baltimore, MD (US)

( * ) Notice: Subject to any disclaimer, the term of this patent is extended or adjusted under 35 U.S.C. 154(b) by 306 days.

(21) Appl. No.: 18/024,417

(22) PCT Filed: Sep. 15, 2021

(86) PCT No.: PCT/US2021/050419
§ 371 (c)(1),
(2) Date: Mar. 2, 2023

(87) PCT Pub. No.: WO2022/060805
PCT Pub. Date: Mar. 24, 2022

(65) Prior Publication Data
US 2023/0265092 A1 Aug. 24, 2023

Related U.S. Application Data

(60) Provisional application No. 63/078,716, filed on Sep. 15, 2020.

(51) Int. Cl.
*C07D 471/04* (2006.01)
*C07D 519/00* (2006.01)

(52) U.S. Cl.
CPC ......... *C07D 471/04* (2013.01); *C07D 519/00* (2013.01)

(58) Field of Classification Search
CPC .................................................... C07D 471/04
See application file for complete search history.

(56) References Cited

U.S. PATENT DOCUMENTS

| | | | |
|---|---|---|---|
| 4,450,150 | A | 5/1984 | Sidman |
| 5,908,840 | A | 6/1999 | Trova et al. |
| 8,680,107 | B2 | 3/2014 | Laiho et al. |
| 10,214,491 | B2 | 2/2019 | Laiho et al. |
| 11,001,581 | B2 | 5/2021 | Laiho et al. |
| 2016/0335737 | A1 | 11/2016 | Shah et al. |
| 2017/0081322 | A1 | 3/2017 | Laiho et al. |
| 2017/0330390 | A1 | 11/2017 | Benavides et al. |
| 2023/0257390 | A1 | 8/2023 | Liu et al. |
| 2023/0265091 | A1 | 8/2023 | Liu et al. |

FOREIGN PATENT DOCUMENTS

| | | | |
|---|---|---|---|
| CA | 2691227 | 12/2008 | |
| CA | 2912456 | 8/2018 | |
| EP | 2195316 | 6/2010 | |
| EP | 2889297 | 7/2015 | |
| WO | WO 2006121767 | 11/2006 | |
| WO | WO 2008155441 | 12/2008 | |
| WO | WO 2005007672 | 1/2015 | |
| WO | WO 2015143293 | 9/2015 | |
| WO | WO-2015143293 A1 * | 9/2015 | ............. A61P 35/00 |
| WO | WO 2018057834 | 3/2018 | |

OTHER PUBLICATIONS

Dorado et al., "Discovery and Evaluation of Novel Angular Fused Pyridoquinazolinonecarboxamides as RNA Polymerase I Inhibitors," Med. Chem. Letters, Mar. 18, 2022, 13(4):608-614.
Extended Search Report in European Appln. No. 21870113.4, mailed on Sep. 18, 2024, 7 pages.
Bruno et al., "A subset of platinum-containing chemotherapeutic agents kills cells by inducing ribosome biogenesis stress," Nature Medicine, Apr. 2017, 23(4):461-471.
Bywater et al., "Inhibition of RNA Polymerase I as a Therapeutic Strategy to Promote Cancer-Specific Activation of p53," Cancer Cell, Jul. 10, 2012, 22(1):51-65.
Carron et al., "Analysis of two human pre-ribosomal factors, bystin and hTsr1, highlights differences in evolution of ribosome biogenesis between yeast and mammals," Nucleic Acids Research, Jan. 2011, 29(1):280-291.
Colis et al., "Design, Synthesis, and Structure-Activity Relationships of Pyridoquinazolinecarboxamides as RNA Polymerase I Inhibitors," Journal of Medicinal Chemistry, Jun. 12, 2014, 57(11):4950-4961.
Colis et al., "DNA intercalator BMH-21 inhibits RNA polymerase I independent of DNA damage response," Oncotarget, May 26, 2014, 5(12):4361-4369.
Connors et al., "Structure-Activity Relationships of the Antitumor Platinum Coordination Complexes," Cancer Treatment Reports, Sep./Oct. 1979, 63(9-10):1499-1502.

(Continued)

*Primary Examiner* — John S Kenyon
*Assistant Examiner* — Rehana Ismail
(74) *Attorney, Agent, or Firm* — Fish & Richardson P.C.

(57) ABSTRACT

This disclosure features chemical entities (e.g., a compound or a pharmaceutically acceptable salt, and/or hydrate, and/or cocrystal, and/or drug combination of the compound) that inhibit RNA polymerase I (Pol I). Said chemical entities are useful, e.g., for treating a condition, disease or disorder in which increased (e.g., excessive) Pol I activity contributes to the pathology and/or symptoms and/or progression of the condition, disease or disorder (e.g., cancer) in a subject (e.g., a human). This disclosure also features compositions containing the same as well as methods of using and making the same.

21 Claims, No Drawings

(56) References Cited

OTHER PUBLICATIONS

Ding et al., "Design of a Platinum-Acridine-Endoxifen Conjugate Targeted at Hormone-Dependent Breast Cancer," Chem Commun (Camb), Mar. 25, 2013, 49(24):2415-2417.
Ding et al., "Using a Build-and-Click Approach for Producing Structural and Functional Diversity in DNA-Targeted Hybrid Anti-cancer Agents," Journal of Medicinal Chemistry, Oct. 17, 2012, 55(22):10198-10203.
Ding et al., "Using Fluorescent Post-Labeling to Probe the Subcellular Localization of DNA-Targeted Platinum," Angewandte Chemie International Edition, Mar. 18, 2013, 52(12):3350-3354.
Dobbelstein et al., "Targeting tumour-supportive cellular machineries in anticancer drug development," Nature Reviews Drug Discovery, Mar. 2014, 13(3):179-196.
Drygin et al., "Anticancer Activity of CX-3543: A Direct Inhibitor of rRNA Biogenesis," Cancer Research, Oct. 1, 2009, 69(19):7653-7661.
Drygin et al., "Targeting RNA Polymerase I with an Oral Small Molecule CX-5461 Inhibits Ribosomal RNA Synthesis and Solid Tumor Growth," Cancer Research, Feb. 15, 2011, 71(4):1418-1430.
Drygin et al., "The RNA Polymerase I Transcription Machinery: An Emerging Target for the Treatment of Cancer," Annual Review of Pharmacology and Toxicology, Oct. 12, 2009, 50:131-156.
Ghezzi et al., "Uptake of antitumor platinum(II)-complexes by cancer cells, assayed by inductively coupled plasma mass spectrometry (ICP-MS)," Journal of Inorganic Biochemistry, Jan. 2004, 98(1):73-78.
Graham et al., "Unusual Reactivity of a Potent Platinum—Acridine Hybrid Antitumor Agent," ACS Medicinal Chemistry Letters, Jun. 25, 2011, 2(9):687-691.
Guner et al., "Novel Assay to Detect RNA Polymerase I Activity In Vivo RNA Hybridization Assay for RNA Pol I Activity," Molecular Cancer Research, May 2017, 15(5):577-584.
Haddach et al., "Discovery of CX-5461, the First Direct and Selective Inhibitor of RNA Polymerase I, for Cancer Therapeutics," ACS Medicinal Chemistry Letters, 2012, 3:602-606.
Hein et al., "The nucleolus: an emerging target for cancer therapy," Trends in Molecular Medicine, Nov. 2013, 19(11):643-654.
Holohan et al., "Cancer drug resistance: an evolving paradigm," Nature Reviews Cancer, Oct. 2013, 13(10):714-726.
Horky et al., "Segregation of nucleolar components coincides with caspase-3 activation in cisplatin-treated HeLa cells," Journal of Cell Science, Feb. 2001, 114(4):663-670.
International Preliminary Report on Patentability in International Application No. PCT/US2021/050412, mailed on Mar. 30, 2023, 8 pages.
International Preliminary Report on Patentability in International Application No. PCT/US2021/050419, mailed on Mar. 30, 2023, 8 pages.
International Preliminary Report on Patentability in International Application No. PCT/US2021/050430, mailed on Mar. 30, 2023, 8 pages.
International Search Report and Written Opinion in International Application No. PCT/US2021/050412, mailed on Dec. 23, 2021, 11 pages.
International Search Report and Written Opinion in International Application No. PCT/US2021/050419, mailed on Dec. 16, 2021, 9 pages.
International Search Report and Written Opinion in International Application No. PCT/US2021/050430, mailed on Dec. 16, 2021, 11 pages.
Johnstone et al., "The Next Generation of Platinum Drugs: Targeted Pt(II) Agents, Nanoparticle Delivery, and Pt(IV) Prodrugs," Chemical Reviews, Feb. 11, 2016, 116(5):3436-3486.
Jordan et al., "Cisplatin inhibits synthesis of ribosomal RNA in vivo," Nucleic Acids Research, Jun. 15, 1998, 26(12):2831-2836.
Khan et al., "Distribution Of Platinum Anti-Tumour Drug in HeLa Cells By Analytical Electron Microscopy," Chemico-Biological Interactions, Jun. 1978, 21(2-3):227-232.
Lefebvre et al., "Copper-Alkyne Complexation Responsible for the Nucleolar Localization of Quadruplex Nucleic Acid Drugs Labeled by Click Reactions," Angewandte Chemie International Edition, Aug. 7, 2017, 56(38):11365-11369.
Liang et al., "Novel nucleolar isolation method reveals rapid response of human nucleolar proteomes to serum stimulation," Journal of Proteomics, Dec. 21, 2012, 77:521-530.
Low et al., "Effective targeting of RNA polymerase I in treatment-resistant prostate cancer," The Prostate, Sep. 16, 2019, 79(16):1837-1851.
Ma et al., "Replacement of a Thiourea-S with an Amidine-NH Donor Group in a Platinum-Acridine Antitumor Compound Reduces the Metal's Reactivity with Cysteine Sulfur," Journal of Medicinal Chemistry, Apr. 27, 2009, 52(10):3424-3427.
Montanaro et al., "The emerging role of RNA polymerase I transcription machinery in human malignancy: a clinical perspective," OncoTargets and Therapy, Jul. 19, 2013, 6:909-916.
Montgomery et al., "Cell-Penetrating Metal Complex Optical Probes: Targeted and Responsive Systems Based on Lanthanide Luminescence," Accounts of Chemical Research, Jul. 2009, 42(7):925-397.
Ozdian et al., "Proteomic profiling reveals DNA damage, nucleolar and ribosomal stress are the main responses to oxaliplatin treatment in cancer cells," Journal of Proteomics, May 3, 2017, 162:73-85.
Peltonen et al., "A targeting modality for destruction of RNA polymerase I that possesses anticancer activity," Cancer Cell, Jan. 13, 2014, 25(1):77-90.
Peltonen et al., "Small Molecule BMH-Compounds That Inhibit RNA Polymerase I and Cause Nucleolar Stress," Molecular Cancer Therapeutics, Nov. 2014, 13(11):2537-2546.
Peterson et al., "Nucleolar Targeting by Platinum: p53-Independent Apoptosis Follows rRNA Inhibition, Cell-Cycle Arrest, and DNA Compaction," Molecular Pharmaceutics, Nov. 18, 2014, 12(1):287-297.
Pickard et al., "Redesigning the DNA-Targeted Chromophore in Platinum-Acridine Anticancer Agents: A Structure-Activity Relationship Study," Chemistry, Dec. 1, 2014, 20(49):16174-16187.
Pickard et al., "The Cell's Nucleolus: an Emerging Target for Chemotherapeutic Intervention," ChemMedChem, Sep. 2013, 8(9):1441-1449.
Qiao et al., "Analysis of the DNA damage produced by a platinum-acridine antitumor agent and its effects in NCI-H460 lung cancer cells," Metallomics, Jul. 2012, 4(7):645-652.
Qiao et al., "Investigating the cellular fate of a DNA-targeted platinum-based anticancer agent by orthogonal double-click chemistry," Journal of Biological Inorganic Chemistry, Jan. 10, 2014, 19:415-426.
Singh et al., "Lanthanoplatins: emissive Eu(III) and Tb(III) complexes staining nucleoli targeted through Pt-DNA crosslinking," Chemical Communications, May 12, 2017, 53:6144-6147.
Suryadi et al., "DNA Metalating-Intercalating Hybrid Agents for the Treatment of Chemoresistant Cancers," Chemistry, Oct. 8, 2012, 18(41):12926-12934.
Tsekrekou et al., "The Nucleolus: In Genome Maintenance and Repair," International Journal of Molecular Sciences, Jul. 1, 2017, 18:1411, 20 pages.
Vlatkovic et al., "Nucleolar control of p53: a cellular Achilles' heel and a target for cancer therapy," Cellular and Molecular Life Sciences, Mar. 2014, 71(5):771-791.
Wedlock et al., "NanoSIMS multi-element imaging reveals internalisation and nucleolar targeting for a highly-charged polynuclear platinum compound," Chemical Communications, May 9, 2013, 49(62):6944-6946.
Wei et al., "Small-molecule targeting of RNA polymerase I activates a conserved transcription elongation checkpoint," Cell Reports, Apr. 10, 2018, 23(2):404-414.
Woods et al., "The nucleolus as a fundamental regulator of the p53 response and a new target for cancer therapy," Biochimica et Biophysica Acta, Jul. 2015, 1849(7):821-829.
Xu et al., "CX-5461 is a DNA G-quadruplex stabilizer with selective lethality in BRCA1/2 deficient tumours," Nature Communications, Feb. 17, 2017, 8:14432, 18 pages.

(56) References Cited

OTHER PUBLICATIONS

Zhang et al., "Targeting RNA polymerase I transcription machinery in cancer cells by a novel monofunctional platinum-based agent," European Journal of Medicinal Chemistry, Jul. 15, 2018, 155:434-444.
STN Registry No. 896688-29-2, "12H-Benzo[g]pyrido[2,1-b]quinazoline-4-carboxamide, N-(2-furanylmethyl)-12-oxo-," dated Jul. 28, 2006, 2 pages.

* cited by examiner

COMPOUNDS WHICH INHIBIT RNA POLYMERASE

CROSS REFERENCE TO RELATED APPLICATION

This application is a National Stage application under 35 U.S.C. § 371 of International Application No. PCT/US2021/050419 having an International Filing Date of Sep. 15, 2021, which claims the benefit of U.S. Provisional Application Ser. No. 63/078,716, filed on Sep. 15, 2020, which is incorporated herein by reference in its entirety.

BACKGROUND

Ribosomal (r) DNA is the most highly transcribed genomic region of the human genome and occurs in a dedicated subcellular compartment, the nucleolus. Transcription of rRNA is mediated by RNA polymerase I (Pol I) that transcribes the multicopy rDNA gene to a long 47S rRNA precursor. The 47S rRNA precursor is processed through multiple steps to the 18S, 5.8S and 28S mature rRNAs requisite for the assembly of the ribosomes. Pol I transcription is initiated by binding of a multisubunit pre-initiation complex to rDNA promoter, which stochastically recruits the Pol I holocomplex. The Pol I holocomplex is composed of 14 subunits in eukaryotes, of which the subunits RPA194, RPA135 and RPA12 form the catalytically active site. Destabilization of the rDNA helix, or loss of the protein framework, will effectively stall transcription. The rate of rRNA transcription is tightly controlled by external signaling pathways that cause the assembly and binding of the preinitiation complex. Deregulation of rRNA synthesis is highly frequent in human cancers. This is due to activation of extracellular and intracellular signaling pathways and oncogenes such as Myc. Conversely, loss-of-function of tumor suppressors p53, pRB, ARF and PTEN lead to activation of Pol I transcription. Therefore, inhibitors of Pol I transcription may provide novel approaches toward cancer therapies.

12H-Benzo[g]pyrido[2,1-b]quinazoline-4-carboxamide, N-[2(dimethylamino)ethyl]-12-oxo (BMH-21) has been shown to exhibit a distinct mode of inhibition of Pol I compared to CX-5461 (see, e.g., U.S. Pat. No. 8,680,107). It is believed that BMH-21 intercalates with GC-rich rDNA, inhibits Pol I and causes proteasome-mediated degradation of RPA194. BMH-21 has also shown anticancer activity in NCI60 cancer cell lines and reduced tumor burden in mouse xenograft assays. WO 2015/143293, filed Mar. 20, 2015, discloses 12-oxo-12H-benzo[g]pyrido[2,1-b]quinazoline-4-carboxamide derivatives that inhibit Pol I.

SUMMARY

This disclosure features chemical entities (e.g., a compound or a pharmaceutically acceptable salt thereof) that inhibit Pol I. Said chemical entities are useful, e.g., for treating a condition, disease or disorder in which increased (e.g., excessive) Pol I activity contributes to the pathology and/or symptoms and/or progression of the condition, disease or disorder (e.g., cancer) in a subject (e.g., a human). This disclosure also features compositions containing the same as well as methods of using and making the same.

In one aspect, this disclosure features compounds of Formula (I):

Formula (I)

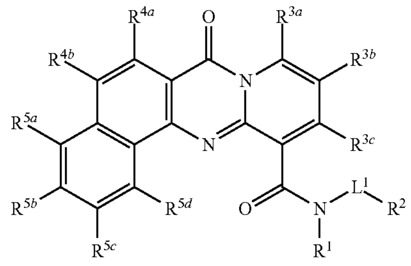

or a pharmaceutically acceptable salt thereof, wherein: $R^1$, $L^1$, $R^2$, $R^{3a}$, $R^{3b}$, $R^{3c}$, $R^{4a}$, $R^{4b}$, $R^{5a}$, $R^{5b}$, $R^{5c}$, and $R^{5d}$ can be as defined elsewhere herein.

In another aspect, this disclosure features pharmaceutical compositions that include one or more compounds of Formula (I), and one or more pharmaceutically acceptable carriers.

In a further aspect, this disclosure features methods for activating upstream p53 pathways in a mammalian cell that include contacting a cell or population of cells with a compound of Formula (I), or a pharmaceutically acceptable salt thereof, or a pharmaceutical composition containing the same.

In still another aspect, this disclosure features methods for modulating RNA Pol I activity in a mammalian cell that include contacting a cell or population of cells with a compound of Formula (I), or a pharmaceutically acceptable salt thereof, or a pharmaceutical composition containing the same In yet a further aspect, this disclosure features methods for treating cancer in a subject in need of such treatment that includes administering to the subject a compound of Formula (I), a pharmaceutically acceptable salt thereof, or a pharmaceutical composition containing the same.

In another aspect, this disclosure features methods for treating cancer in a subject in need thereof that includes administering to the subject a compound of Formula (I), or a pharmaceutically acceptable salt thereof, or a pharmaceutical composition containing the same, and at least one additional therapeutic agent.

In one aspect, this disclosure features methods for treating an autoimmune disease or disorder in a subject in need thereof that includes administering to the subject a compound of Formula (I), or a pharmaceutically acceptable salt thereof, or a pharmaceutical composition containing the same.

In another aspect, this disclosure features methods for treating a condition associated with inflammation or pain in a subject in need thereof that includes administering to the subject a compound of Formula (I), or a pharmaceutically acceptable salt thereof, or a pharmaceutical composition containing the same.

In certain of the foregoing embodiments, the methods further include administering to the subject one or more additional therapeutic agents.

DETAILED DESCRIPTION

This disclosure features chemical entities (e.g., a compound or a pharmaceutically acceptable salt thereof) that inhibit Pol I. Said chemical entities are useful, e.g., for treating a condition, disease or disorder in which increased (e.g., excessive) Pol I activity contributes to the pathology and/or symptoms and/or progression of the condition, disease or disorder (e.g., cancer) in a subject (e.g., a human). This disclosure also features compositions containing the same as well as methods of using and making the same.

In one aspect, the present disclosure features compounds of Formula (I):

Formula (I)

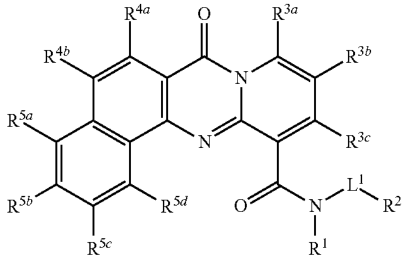

or a pharmaceutically acceptable salt thereof, wherein:

$R^1$ is H or $C_{1-3}$ alkyl;

$R^2$ is selected from the group consisting of:

(a) —$NR^6R^7$, wherein $R^6$ and $R^7$ are independently selected from the group consisting of: H and $C_{1-6}$ alkyl which is optionally substituted with from 1-6 $R^a$;

(b) —$OR^8$, wherein $R^8$ is H or $C_{1-6}$ alkyl which is optionally substituted with from 1-6 $R^a$; and (c) heterocyclyl including from 4-12 ring atoms, wherein from 1-3 ring atoms are ring heteroatoms each independently selected from the group consisting of N, NH, $N(R^d)$, O, and $S(O)_{0-2}$, wherein the heterocyclyl is optionally substituted with from 1-6 $R^b$;

$L^1$ is a bond or $C_{1-6}$ alkylene which is optionally substituted with from 1-6 $R^c$, provided that when $L^1$ is a bond, then $R^2$ is heterocyclyl that is attached to $L^1$ via a ring carbon atom;

$R^{3a}$, $R^{3b}$, $R^{3c}$, $R^{4a}$, $R^{4b}$, $R^{5a}$, $R^{5b}$, $R^{5c}$, and $R^{5d}$ are each independently selected from the group consisting of: H, halo, $C_{1-6}$ alkyl, $C_{1-6}$ haloalkyl, $C_{1-6}$ alkoxy, $C_{1-6}$ haloalkoxy, and OH;

each occurrence of $R^a$ and $R^c$ is independently selected from the group consisting of: —OH; -halo; —NR'R"; $C_{1-4}$ alkoxy; $C_{1-4}$ haloalkoxy; —C(═O)O($C_{1-4}$ alkyl); —C(═O)($C_{1-4}$ alkyl); —C(═O)OH; —CONR'R"; —$S(O)_{1-2}$NR'R"; —$S(O)_{1-2}$($C_{1-4}$ alkyl); and cyano;

each occurrence of $R^b$ is independently selected from the group consisting of: $C_{1-6}$ alkyl; $C_{1-6}$ haloalkyl; oxo; —OH; -halo; —NR'R"; $C_{1-4}$ alkoxy; $C_{1-4}$ haloalkoxy; —C(═O)O($C_{1-4}$ alkyl); —C(═O)($C_{1-4}$ alkyl); —C(═O)OH; —CONR'R"; —$S(O)_{1-2}$NR'R"; —$S(O)_{1-2}$($C_{1-4}$ alkyl); and cyano;

each occurrence of $R^d$ is independently $C_{1-6}$ alkyl; —C(O)($C_{1-4}$ alkyl); or —C(O)O($C_{1-4}$ alkyl); and each occurrence of R' and R" is independently H or $C_{1-3}$ alkyl.

As used herein, the term "halo" refers to fluoro (F), chloro (Cl), bromo (Br), or iodo (I).

As used herein, the term "alkyl" refers to a hydrocarbon chain that may be a straight chain or branched chain, containing the indicated number of carbon atoms. For example, $C_{1-10}$ indicates that the group may have from 1 to 10 (inclusive) carbon atoms in it. Non-limiting examples include methyl, ethyl, iso-propyl, tert-butyl, n-hexyl.

As used herein, the term "haloalkyl" refers to an alkyl, in which one or more hydrogen atoms is/are replaced with an independently selected halo.

As used herein, the term "alkoxy" refers to an —O-alkyl radical (e.g., —$OCH_3$). Accordingly, the term "haloalkoxy" refers to an —O-haloalkyl radical (e.g., —$OCF_3$).

As used herein, the term "alkylene" refers to a divalent alkyl (e.g., —$CH_2$—).

As used herein, the term "heterocyclyl" refers to a mono-, bi-, tri-, or polycyclic nonaromatic ring system with 3-16 ring atoms (e.g., 5-8 membered monocyclic, 8-12 membered bicyclic, or 11-14 membered tricyclic ring system) having 1-3 heteroatoms if monocyclic, 1-6 heteroatoms if bicyclic, or 1-9 heteroatoms if tricyclic or polycyclic, said heteroatoms selected from O, N, or $S(O)_{0-2}$ (e.g., carbon atoms and 1-3, 1-6, or 1-9 heteroatoms of N, O, or $S(O)_{0-2}$ if monocyclic, bicyclic, or tricyclic, respectively), wherein 0, 1, 2 or 3 atoms of each ring may be substituted by a substituent. Examples of heterocyclyl groups include piperazinyl, pyrrolidinyl, dioxanyl, morpholinyl, tetrahydrofuranyl, and the like. Heterocyclyl may include multiple fused and bridged rings. Non-limiting examples of fused/bridged heteorocyclyl includes: 2-azabicyclo[1.1.0]butane, 2-azabicyclo[2.1.0]pentane, 2-azabicyclo[1.1.1]pentane, 3-azabicyclo[3.1.0]hexane, 5-azabicyclo[2.1.1]hexane, 3-azabicyclo[3.2.0]heptane, octahydrocyclopenta[c]pyrrole, 3-azabicyclo[4.1.0]heptane, 7-azabicyclo[2.2.1]heptane, 6-azabicyclo[3.1.1]heptane, 7-azabicyclo[4.2.0]octane, 2-azabicyclo[2.2.2]octane, 3-azabicyclo[3.2.1]octane, 2-oxabicyclo[1.1.0]butane, 2-oxabicyclo[2.1.0]pentane, 2-oxabicyclo[1.1.1]pentane, 3-oxabicyclo[3.1.0]hexane, 5-oxabicyclo[2.1.1]hexane, 3-oxabicyclo[3.2.0]heptane, 3-oxabicyclo[4.1.0]heptane, 7-oxabicyclo[2.2.1]heptane, 6-oxabicyclo[3.1.1]heptane, 7-oxabicyclo[4.2.0]octane, 2-oxabicyclo[2.2.2]octane, 3-oxabicyclo[3.2.1]octane, and the like. Heterocyclyl also includes spirocyclic rings (e.g., spirocyclic bicycle wherein two rings are connected through just one atom). Non-limiting examples of spirocyclic heterocyclyls include 2-azaspiro[2.2]pentane, 4-azaspiro[2.5]octane, 1-azaspiro[3.5]nonane, 2-azaspiro[3.5]nonane, 7-azaspiro[3.5]nonane, 2-azaspiro[4.4]nonane, 6-azaspiro[2.6]nonane, 1,7-diazaspiro[4.5]decane, 7-azaspiro[4.5]decane 2,5-diazaspiro[3.6]decane, 3-azaspiro[5.5]undecane, 2-oxaspiro[2.2]pentane, 4-oxaspiro[2.5]octane, 1-oxaspiro[3.5]nonane, 2-oxaspiro[3.5]nonane, 7-oxaspiro[3.5]nonane, 2-oxaspiro[4.4]nonane, 6-oxaspiro[2.6]nonane, 1,7-dioxaspiro[4.5]decane, 2,5-dioxaspiro[3.6]decane, 1-oxaspiro[5.5]undecane, 3-oxaspiro[5.5]undecane, 3-oxa-9-azaspiro[5.5]undecane and the like.

Included within the compounds of the present disclosure are the tautomeric forms of the disclosed compounds, isomeric forms including diastereoisomers, and the pharmaceutically acceptable salts thereof.

Certain compounds of the present disclosure possess asymmetric carbon atoms (optical or chiral centers) or double bonds; the enantiomers, racemates, diastereomers, tautomers, geometric isomers, stereoisomeric forms that may be defined, in terms of absolute stereochemistry, as (R)- or (S)-, and individual isomers are encompassed within the scope of the disclosure. The compounds of the present disclosure do not include those which are known in art to be too unstable to synthesize and/or isolate. The disclosure is meant to include compounds in racemic and optically pure forms. Optically active (R)- and (S)-, isomers may be prepared using chiral synthons or chiral reagents as disclosed herein, or resolved using conventional techniques. When the compounds described herein contain olefinic bonds or other centers of geometric asymmetry, and unless specified otherwise, it is intended that the compounds include both E and Z geometric isomers.

In some embodiments, $L^1$ is $C_{1-6}$ (e.g., $C_1$, $C_2$, $C_3$, $C_4$, $C_5$, or $C_6$) alkylene optionally substituted with from 1-6 $R^c$ (e.g., unsubstituted or substituted with 1, 2, 3, or 4 $R^c$).

In certain of these embodiments, $L^1$ is unsubstituted $C_{1-4}$ alkylene.

In certain embodiments, $L^1$ is an unsubstituted linear $C_{1-4}$ alkylene, such as $—CH_2—$, $—CH_2CH_2—$, or $—CH_2CH_2CH_2—$.

As a non-limiting example, $L^1$ can be $CH_2CH_2$.

In certain embodiments, $L^1$ is an unsubstituted branched $C_{3-4}$ alkylene. In certain of these embodiments, $L^1$ comprises a stereogenic center. In certain of these embodiments, the stereogenic center has (S)-configuration. In certain embodiments, the stereogenic center has (R)-configuration.

In certain embodiments (when $L^1$ is an unsubstituted branched $C_{3-4}$ alkylene), $L^1$ is selected from the group consisting of:

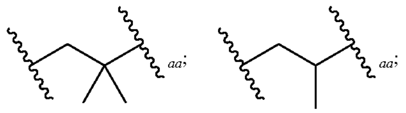

(e.g., 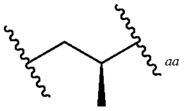 or 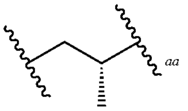);

and

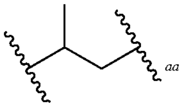

(e.g., 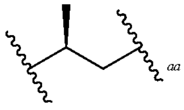 or 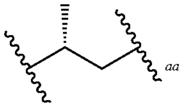).

wherein aa is the point of attachment to $R^2$.

As a non-limiting example, $L^1$ can be

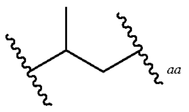

(e.g., 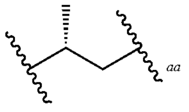).

In some embodiments, $L^1$ is a bond.

In some embodiments, $R^2$ is $NR^6R^7$.

In certain of these embodiments, $R^2$ is selected from the group consisting of: $NH(C_{1-3}$ alkyl) and $N(C_{1-3}$ alkyl$)_2$.

As a non-limiting example of the foregoing embodiments, $R^2$ can be $NH_2$, NHMe, $NMe_2$, NMeEt, or $NEt_2$.

For example, $R^2$ can be $NMe_2$.

In some embodiments, $R^2$ is $—OR^8$. For example, $R^2$ can be —OH.

In some embodiments, $R^2$ is heterocyclyl including from 4-12 (e.g., 4, 5, 6, 7, 8, 9, or 10) ring atoms, wherein from 1-3 (e.g., 1, 2, or 3) ring atoms are ring heteroatoms each independently selected from the group consisting of N, NH, $N(R^d)$, O, and $S(O)_{0-2}$, wherein the heterocyclyl is optionally substituted with from 1-6 (e.g., 1, 2, or 3) $R^b$.

In certain of these embodiments, $R^2$ is heterocyclyl including from 4-8 ring atoms, wherein from 1-2 ring atoms are ring heteroatoms each independently selected from the group consisting of N, NH, $N(R^d)$, O, and $S(O)_{0-2}$, wherein the heterocyclyl is optionally substituted with from 1-6 $R^b$, wherein at least 1 ring atom is N, NH, or $N(R^d)$.

In certain embodiments, $R^2$ is selected from the group consisting of azetidinyl, pyrrolidinyl, piperidinyl, or 8-oxa-3-azabicyclo[3.2.1]octanyl, each of which is optionally substituted with from 1-2 $R^b$.

In certain embodiments, $R^2$ is azetidinyl which is optionally substituted with from 1-2 $R^b$, wherein the ring nitrogen is optionally substituted with $R^d$. For example, $R^2$ can be

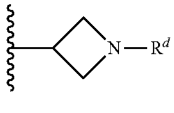

(e.g., 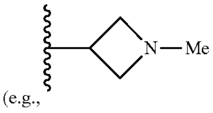).

In certain embodiments, $R^2$ is pyrrolidinyl which is optionally substituted with from 1-2 $R^b$. For example, $R^2$ is

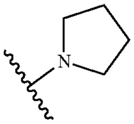,

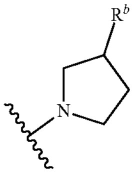

(e.g., 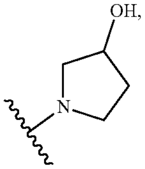

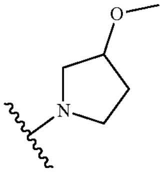,

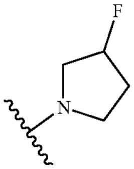),

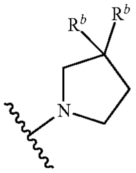

(e.g., 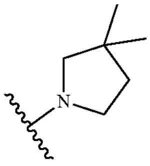)

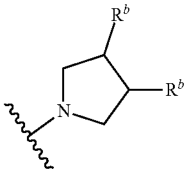

(e.g., 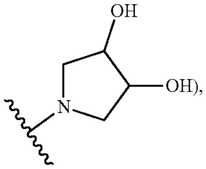), or

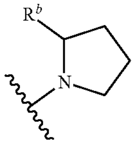

(e.g., 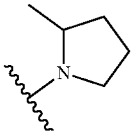)

In certain embodiments, $R^2$ is

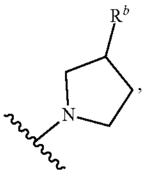, such as

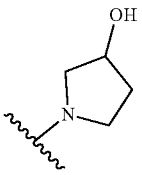

(e.g.,

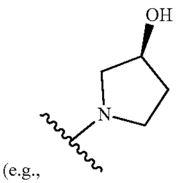

or

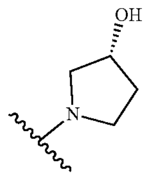

).

In certain embodiments, $R^2$ is

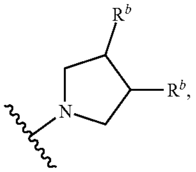

such as

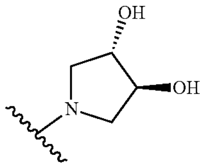

or

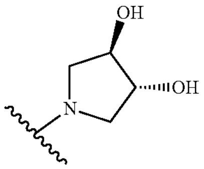

In certain embodiments, $R^2$ is piperidinyl, which is optionally substituted with from 1-2 $R^b$. For example, $R^2$ is

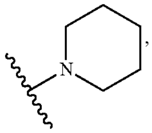

,

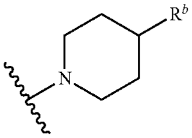

(e.g.,

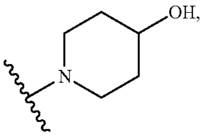

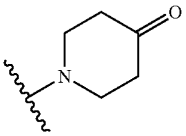

)

In certain embodiments, $R^2$ is a 8-oxa-3-azabicyclo[3.2.1] octanyl, which is optionally substituted with from 1-2 $R^b$. For example, $R^2$ is

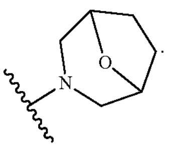 [SMILES: *N1CC2CCC(C1)O2]

In some embodiments, each $R^b$ is independently selected from the group consisting of: halo (such as —F); —OH; oxo; $C_{1-3}$ alkyl (e.g., methyl); and $C_{1-3}$ alkoxy (e.g., methoxy).

In some embodiments, $R^1$ is H.

In some embodiments, $R^{3a}$ is H.

In some embodiments, $R^{3b}$ is H.

In some embodiments, $R^{3c}$ is H.

In some embodiments, $R^{4a}$ is H.

In some embodiments, $R^{4b}$ is H.

In some embodiments, $R^{5a}$ is H.

In some embodiments, $R^{5b}$ is H.

In some embodiments, $R^{5c}$ is H.

In some embodiments, $R^{5d}$ is H.

In certain embodiments, $R^{3a}$, $R^{3b}$, $R^{3c}$, $R^{4a}$, $R^{4b}$, $R^{5a}$, $R^{5b}$, $R^{5c}$, and $R^{5d}$ are each H.

In some embodiments, from 0-4 (e.g., 0, 1, 2, or 3) of $R^{3a}$, $R^{3b}$, $R^{3c}$, $R^{4a}$, $R^{4b}$, $R^{5a}$, $R^{5b}$, $R^{5c}$, and $R^{5d}$ is other than H; and each remaining of $R^{3a}$, $R^{3b}$, $R^{3c}$, $R^{4a}$, $R^{4b}$, $R^{5a}$, $R^{5b}$, $R^{5c}$, and $R^{5d}$ is H.

Non-Limiting Combination [AA]:

In some embodiments, $R^1$ is H; $L^1$ is $—CH_2CH_2—$ or

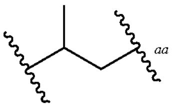

wherein aa is the point of attachment to $R^2$; and $R^2$ is $N(C_{1-3}\ alkyl)_2$ or $R^2$ is pyrrolidinyl which is optionally substituted with from 1-2 $R^b$, wherein the ring nitrogen is optionally substituted with $R^d$.

In certain embodiments of [AA], $L^1$ is $—CH_2CH_2—$.

In certain embodiments of [AA], $L^1$ is

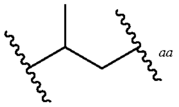

(e.g.,

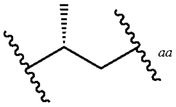

).

In certain embodiments of [AA], $R^2$ is $N(C_{1-3}\ alkyl)_2$, such as $NMe_2$.

In certain embodiments of [AA], $R^2$ is pyrrolidinyl which is optionally substituted with from 1-2 $R^b$, wherein the ring nitrogen is optionally substituted with $R^d$. For example, $R^2$ can be

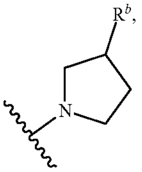

such as

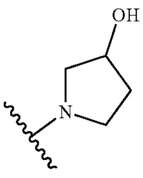

(e.g.,

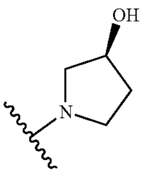

or

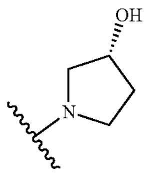

).

In certain embodiments of [AA], $R^{3a}$, $R^{3b}$, $R^{3c}$, $R^{4a}$, $R^{4b}$, $R^{5a}$, $R^{5b}$, $R^{5c}$, and $R^{5d}$ are each H.

In some embodiments, the compound of Formula (I) is selected from the group consisting of the compounds in Table C1, or a pharmaceutically acceptable salt thereof.
TABLE C1
| Compound No. | Structure |
|---|---|
| 101 | 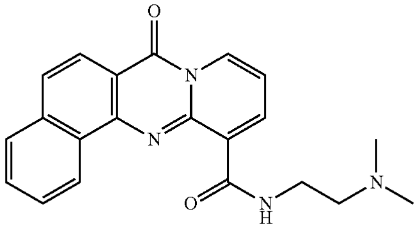 [SMILES: CN(C)CCNC(=O)c1cccn2c(=O)c3ccc4ccccc4c3nc12] |
| 102 | 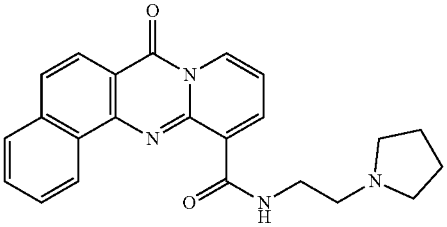 [SMILES: O=C(NCCN1CCCC1)c1cccn2c(=O)c3ccc4ccccc4c3nc12] |
| 103 | 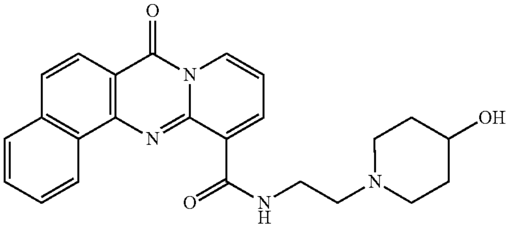 [SMILES: O=C(NCCN1CCC(O)CC1)c1cccn2c(=O)c3ccc4ccccc4c3nc12] |
| 104 | 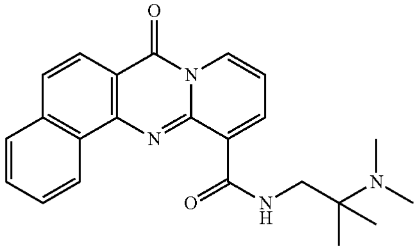 [SMILES: CN(C)C(C)(C)CNC(=O)c1cccn2c(=O)c3ccc4ccccc4c3nc12] |
| 105 | 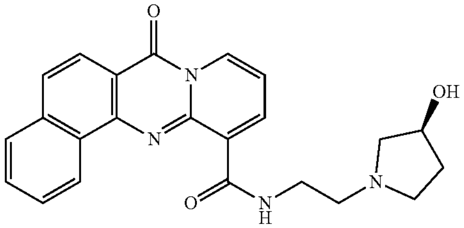 |
| 106 | 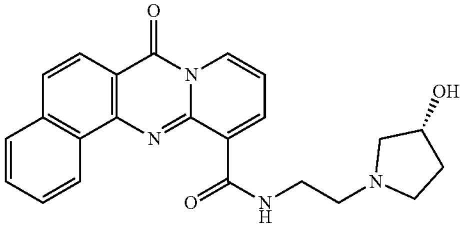 [SMILES: O=C(NCCN1CC[C@@H](O)C1)c1cccn2c(=O)c3ccc4ccccc4c3nc12] |
TABLE C1-continued
| Compound No. | Structure |
|---|---|
| 107 | 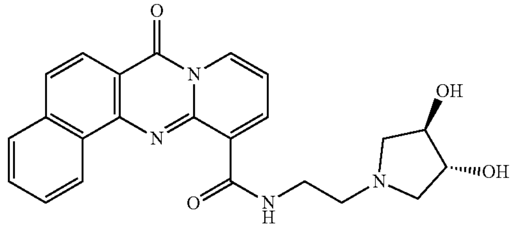 [SMILES: O=C(NCCN1C[C@@H](O)[C@H](O)C1)c1cccn2c(=O)c3ccc4ccccc4c3nc12] |
| 108 | 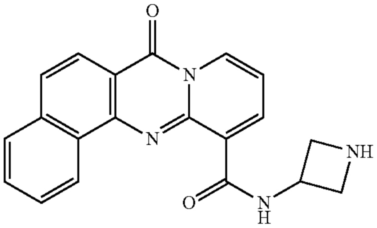 [SMILES: O=C(NC1CNC1)c1cccn2c(=O)c3ccc4ccccc4c3nc12] |
| 109 | 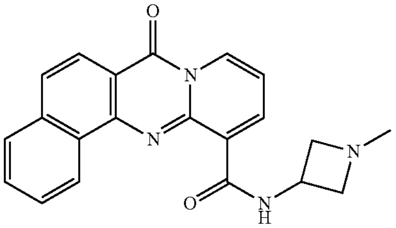 [SMILES: CN1CC(NC(=O)c2cccn3c(=O)c4ccc5ccccc5c4nc23)C1] |
| 110 | 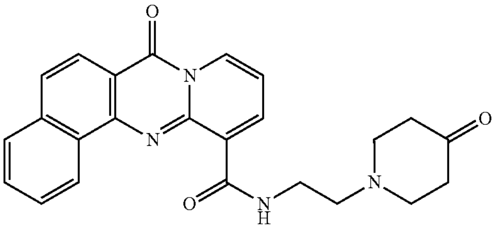 [SMILES: O=C1CCN(CCNC(=O)c2cccn3c(=O)c4ccc5ccccc5c4nc23)CC1] |
| 111 | 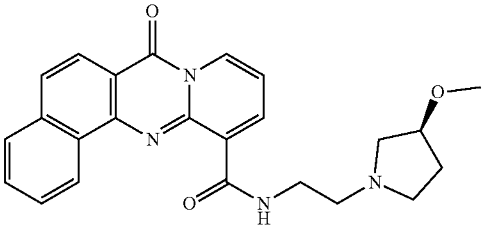 [SMILES: CO[C@H]1CCN(CCNC(=O)c2cccn3c(=O)c4ccc5ccccc5c4nc23)C1] |
| 112 | 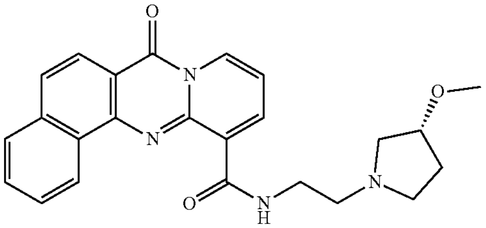 [SMILES: CO[C@@H]1CCN(CCNC(=O)c2cccn3c(=O)c4ccc5ccccc5c4nc23)C1] |

TABLE C1-continued
| Compound No. | Structure |
|---|---|
| 113 | 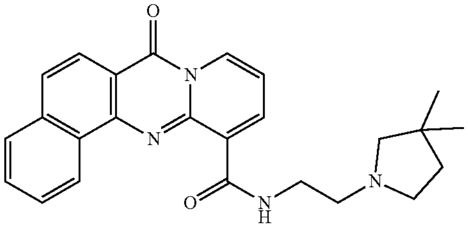 [SMILES: CC1(C)CCN(CCNC(=O)c2cccn3c(=O)c4ccc5ccccc5c4nc23)C1] |
| 114 | 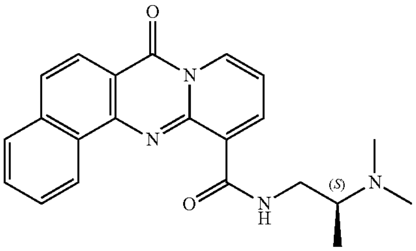 |
| 115 | 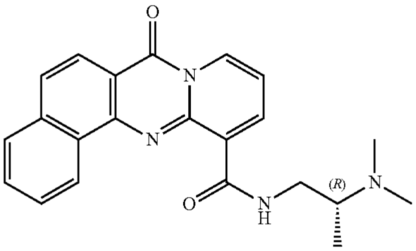 |
| 116 | 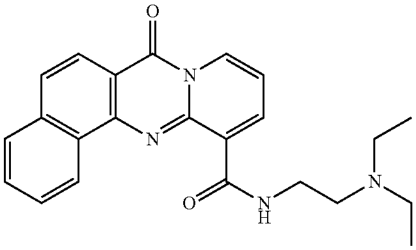 [SMILES: CCN(CC)CCNC(=O)c1cccn2c(=O)c3ccc4ccccc4c3nc12] |
| 117 | 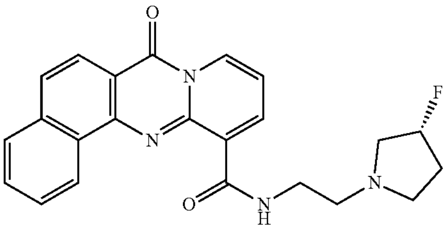 [SMILES: O=C(NCCN1CC[C@@H](F)C1)c1cccn2c(=O)c3ccc4ccccc4c3nc12] |
| 118 | 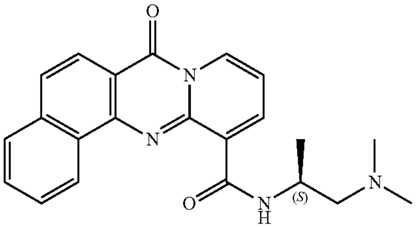 |
TABLE C1-continued
| Compound No. | Structure |
|---|---|
| 119 | 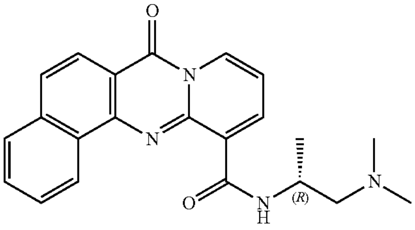 |
| 120 | 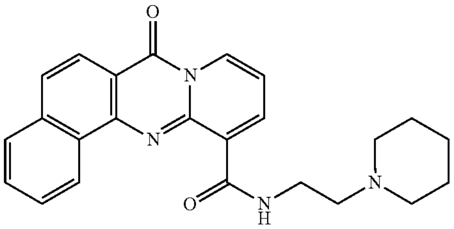 [SMILES: O=C(NCCN1CCCCC1)c1cccn2c(=O)c3ccc4ccccc4c3nc12] |
| 121 | 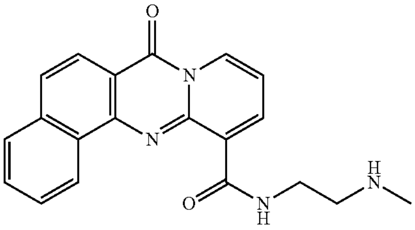 |
| 122 | 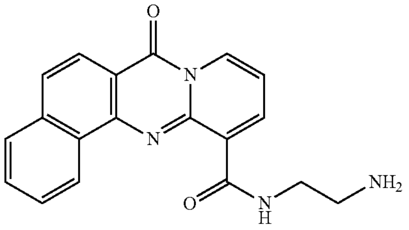 [SMILES: NCCNC(=O)c1cccn2c(=O)c3ccc4ccccc4c3nc12] |
| 123 | 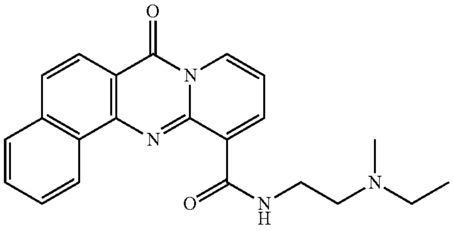 [SMILES: CCN(C)CCNC(=O)c1cccn2c(=O)c3ccc4ccccc4c3nc12] |
| 124 | 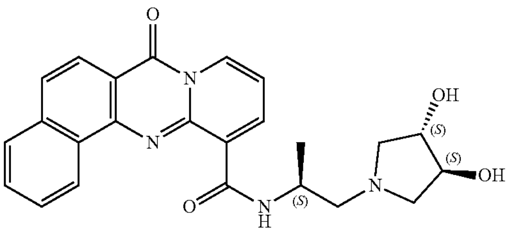 |

| Compound No. | Structure |
|---|---|
| 125 | 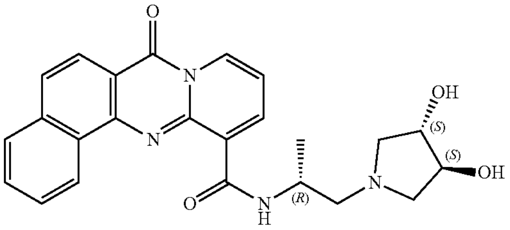 |
| 126 | 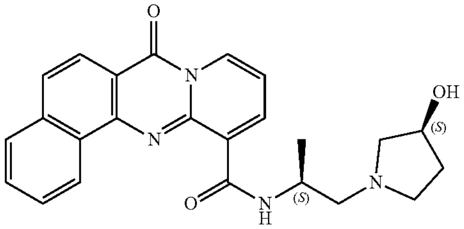 |
| 127 | 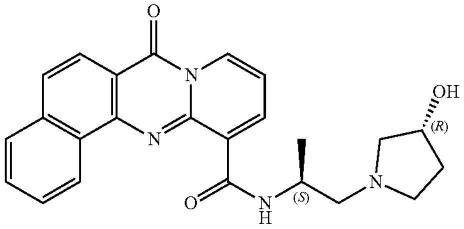 |
| 128 | 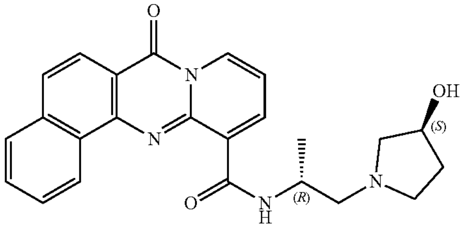 |
| 129 | 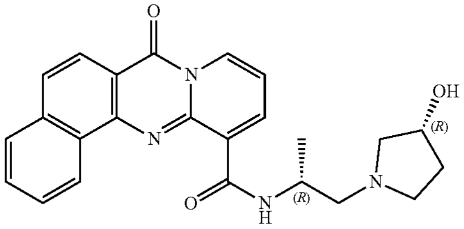 |
| 130 | 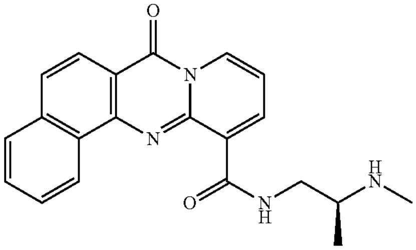 [SMILES: CN[C@@H](C)CNC(=O)c1cccn2c(=O)c3ccc4ccccc4c3nc12] |
| Compound No. | Structure |
|---|---|
| 131 | 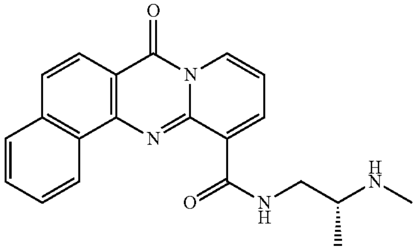 [SMILES: CN[C@H](C)CNC(=O)c1cccn2c(=O)c3ccc4ccccc4c3nc12] |
| 132 | 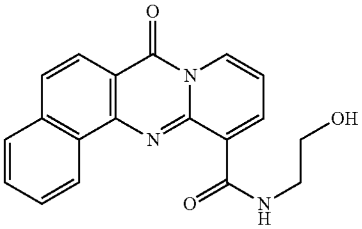 [SMILES: O=C(NCCO)c1cccn2c(=O)c3ccc4ccccc4c3nc12] |
| 133 | 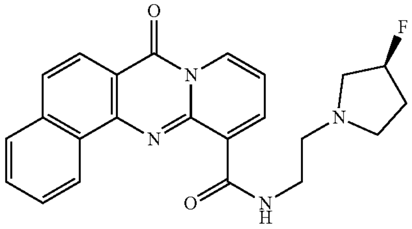 [SMILES: O=C(NCCN1CC[C@H](F)C1)c1cccn2c(=O)c3ccc4ccccc4c3nc12] |
| 134 | 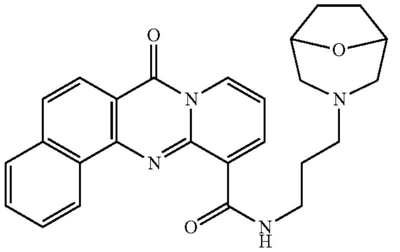 [SMILES: O=C(NCCCN1CC2CCC(C1)O2)c1cccn2c(=O)c3ccc4ccccc4c3nc12] |
| 135 | 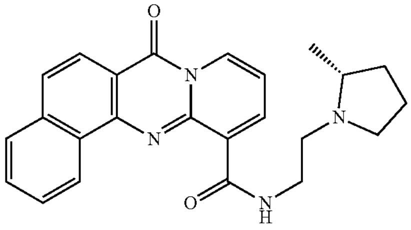 [SMILES: C[C@@H]1CCCN1CCNC(=O)c1cccn2c(=O)c3ccc4ccccc4c3nc12] |
| 136 | 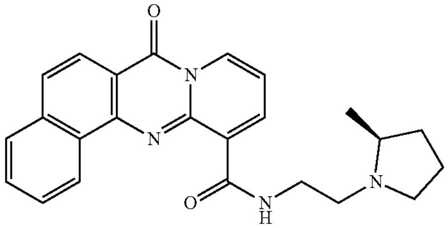 [SMILES: C[C@H]1CCCN1CCNC(=O)c1cccn2c(=O)c3ccc4ccccc4c3nc12] |

TABLE C1-continued

| Compound No. | Structure |
|---|---|
| 137 | 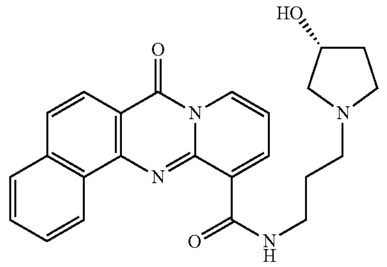 [SMILES: O=C(NCCCN1CC[C@@H](O)C1)c1cccn2c(=O)c3ccc4ccccc4c3nc12] |
| 138 | 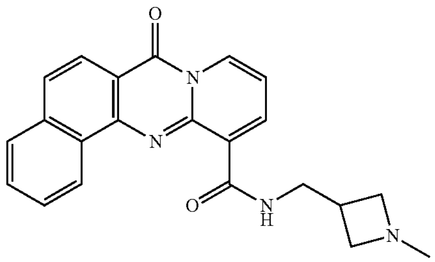 [SMILES: CN1CC(CNC(=O)c2cccn3c(=O)c4ccc5ccccc5c4nc23)C1] |
| 139 | 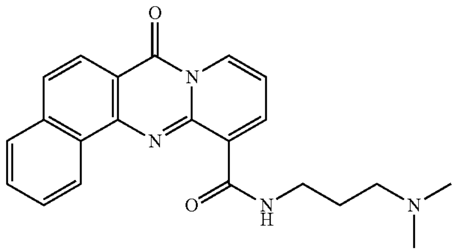 [SMILES: CN(C)CCCNC(=O)c1cccn2c(=O)c3ccc4ccccc4c3nc12] |
| 140 | 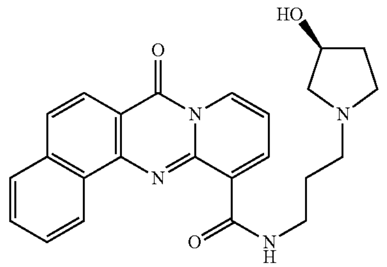 [SMILES: O=C(NCCCN1CC[C@H](O)C1)c1cccn2c(=O)c3ccc4ccccc4c3nc12] |

The term "pharmaceutically acceptable salts" embraces salts commonly used to form alkali metal salts and to form addition salts of free acids or free bases. Examples of acids which may be employed to form pharmaceutically acceptable acid addition salts include such inorganic acids as hydrochloric acid, sulphuric acid and phosphoric acid, and such organic acids as maleic acid, succinic acid and citric acid. Other pharmaceutically acceptable salts include salts with alkali metals or alkaline earth metals, such as sodium, potassium, calcium and magnesium, or with organic bases, such as dicyclohexylamine. Suitable pharmaceutically acceptable salts of the compounds of the disclosure include, for example, acid addition salts which may, for example, be formed by mixing a solution of the compound according to the disclosure with a solution of a pharmaceutically acceptable acid, such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. All of these salts may be prepared by conventional means by reacting, for example, the appropriate acid or base with the corresponding compounds of the present disclosure.

Salts formed from free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

For use in medicines, the salts of the compounds of the present disclosure should be pharmaceutically acceptable salts. Other salts may, however, be useful in the preparation of the compounds according to the disclosure or of their pharmaceutically acceptable salts.

In addition, embodiments of the disclosure include hydrates of the compounds of the present disclosure. The term "hydrate" includes but is not limited to hemihydrate, monohydrate, dihydrate, trihydrate and the like. Hydrates of the compounds of the present disclosure may be prepared by contacting the compounds with water under suitable conditions to produce the hydrate of choice.

In one aspect, the present disclosure provides pharmaceutical compositions comprising the compounds of Formula (I), or their salts, solvates, or stereoisomers thereof, and a pharmaceutically acceptable carrier.

Embodiments of the disclosure also include a process for preparing pharmaceutical products comprising the compounds. The term "pharmaceutical product" means a composition suitable for pharmaceutical use (pharmaceutical composition), as defined herein. Pharmaceutical compositions formulated for particular applications comprising the compounds of the present disclosure are also part of this disclosure, and are to be considered an embodiment thereof.

As such, in another aspect, the present disclosure provides a pharmaceutical composition comprising the compound of Formula (I) and a pharmaceutically acceptable carrier. In some embodiments, the pharmaceutical composition can further comprise at least one additional therapeutic agent.

In another aspect, the present disclosure provides a pharmaceutical composition comprising a compound of Formula (I) and a pharmaceutically acceptable carrier, in an effective amount, for use as a medicament, e.g., for use in inhibiting RNA Pol I in a mammalian cell or population of cells, or for use in treating cancer in a subject.

With respect to pharmaceutical compositions described herein, the pharmaceutically acceptable carrier can be any of those conventionally used, and is limited only by physico-chemical considerations, such as solubility and lack of reactivity with the active compound(s), and by the route of administration. The pharmaceutically acceptable carriers described herein, for example, vehicles, adjuvants, excipients, and diluents, are well-known to those skilled in the art and are readily available to the public. Examples of the pharmaceutically acceptable carriers include soluble carriers such as known buffers which can be physiologically acceptable (e.g., phosphate buffer) as well as solid compositions such as solid-state carriers or latex beads. It is preferred that the pharmaceutically acceptable carrier be one which is chemically inert to the active agent(s), and one which has little or no detrimental side effects or toxicity under the conditions of use.

The carriers or diluents used herein may be solid carriers or diluents for solid formulations, liquid carriers or diluents for liquid formulations, or mixtures thereof.

Solid carriers or diluents include, but are not limited to, gums, starches (e.g., corn starch, pregelatinized starch), sugars (e.g., lactose, mannitol, sucrose, dextrose), cellulosic materials (e.g., microcrystalline cellulose), acrylates (e.g., polymethylacrylate), calcium carbonate, magnesium oxide, talc, or mixtures thereof.

For liquid formulations, pharmaceutically acceptable carriers may be, for example, aqueous or non-aqueous solutions, suspensions, emulsions or oils. Examples of non-aqueous solvents are propylene glycol, polyethylene glycol, and injectable organic esters such as ethyl oleate. Aqueous carriers include, for example, water, alcoholic/aqueous solutions, cyclodextrins, emulsions or suspensions, including saline and buffered media.

Examples of oils are those of petroleum, animal, vegetable, or synthetic origin, for example, peanut oil, soybean oil, mineral oil, olive oil, sunflower oil, fish-liver oil, sesame oil, cottonseed oil, corn oil, olive, petrolatum, and mineral. Suitable fatty acids for use in parenteral formulations include, for example, oleic acid, stearic acid, and isostearic acid. Ethyl oleate and isopropyl myristate are examples of suitable fatty acid esters.

Parenteral vehicles (for subcutaneous, intravenous, intraarterial, or intramuscular injection) include, for example, sodium chloride solution, Ringer's dextrose, dextrose and sodium chloride, lactated Ringer's and fixed oils. Formulations suitable for parenteral administration include, for example, aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

Intravenous vehicles include, for example, fluid and nutrient replenishers, electrolyte replenishers such as those based on Ringer's dextrose, and the like. Examples are sterile liquids such as water and oils, with or without the addition of a surfactant and other pharmaceutically acceptable adjuvants. In general, water, saline, aqueous dextrose and related sugar solutions, and glycols such as propylene glycols or polyethylene glycol are preferred liquid carriers, particularly for injectable solutions.

In addition, in an embodiment, the compounds of the present disclosure may further comprise, for example, binders (e.g., acacia, cornstarch, gelatin, carbomer, ethyl cellulose, guar gum, hydroxypropyl cellulose, hydroxypropyl methyl cellulose, povidone), disintegrating agents (e.g., cornstarch, potato starch, alginic acid, silicon dioxide, croscarmelose sodium, crospovidone, guar gum, sodium starch glycolate), buffers (e.g., Tris-HCl, acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g. sodium lauryl sulfate), permeation enhancers, solubilizing agents (e.g., cremophor, glycerol, polyethylene glycerol, benzlkonium chloride, benzyl benzoate, cyclodextrins, sorbitan esters, stearic acids), anti-oxidants (e.g., ascorbic acid, sodium metabisulfite, butylated hydroxyanisole), stabilizers (e.g., hydroxypropyl cellulose, hydroxypropylmethyl cellulose), viscosity increasing agents (e.g., carbomer, colloidal silicon dioxide, ethyl cellulose, guar gum), sweetners (e.g., aspartame, citric acid), preservatives (e.g., thimerosal, benzyl alcohol, parabens), lubricants (e.g., stearic acid, magnesium stearate, polyethylene glycol, sodium lauryl sulfate), flow-aids (e.g., colloidal silicon dioxide), plasticizers (e.g., diethyl phthalate, triethyl citrate), emulsifiers (e.g., carbomer, hydroxypropyl cellulose, sodium lauryl sulfate), polymer coatings (e.g., poloxamers or poloxamines), coating and film forming agents (e.g., ethyl cellulose, acrylates, polymethacrylates), and/or adjuvants.

The choice of carrier will be determined, in part, by the particular compound, as well as by the particular method used to administer the compound. Accordingly, there are a variety of suitable formulations of the pharmaceutical composition of the disclosure. The following formulations for parenteral, subcutaneous, intravenous, intramuscular, intraarterial, intrathecal and interperitoneal administration are exemplary, and are in no way limiting. More than one route can be used to administer the compounds, and in certain instances, a particular route can provide a more immediate and more effective response than another route.

Suitable soaps for use in parenteral formulations include, for example, fatty alkali metal, ammonium, and triethanolamine salts, and suitable detergents include, for example, (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-Q-aminopropionates, and 2-alkyl-imidazoline quaternary ammonium salts, and (e) mixtures thereof.

The parenteral formulations will typically contain from about 0.5% to about 25% by weight of the compounds in solution. Preservatives and buffers may be used. In order to minimize or eliminate irritation at the site of injection, such compositions may contain one or more nonionic surfactants, for example, having a hydrophile-lipophile balance (HLB) of from about 12 to about 17. The quantity of surfactant in such formulations will typically range from about 5% to about 15% by weight. Suitable surfactants include, for example, polyethylene glycol sorbitan fatty acid esters, such as sorbitan monooleate and the high molecular weight adducts of ethylene oxide with a hydrophobic base, formed by the condensation of propylene oxide with propylene glycol.

The parenteral formulations can be presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets.

Injectable formulations are in accordance with the disclosure. The requirements for effective pharmaceutical carriers for injectable compositions are well-known to those of ordinary skill in the art (see, e.g., *Pharmaceutics and Pharmacy Practice*, J. B. Lippincott Company, Philadelphia, PA, Banker and Chalmers, eds., pages 238-250 (1982), and *ASHP Handbook on Injectable Drugs*, Trissel, 15th ed., pages 622-630 (2009)).

In some embodiments, the chemical entities described herein or a pharmaceutical composition thereof are suitable for local and topical administration to the eye (e.g., eye drops). Ocular compositions can include, without limitation, one or more of any of the following: viscogens (e.g., Carboxymethylcellulose, Glycerin, Polyvinylpyrrolidone, Polyethylene glycol); Stabilizers (e.g., Pluronic (triblock copolymers), Cyclodextrins); Preservatives (e.g., Benzalkonium chloride, ETDA, SofZia (boric acid, propylene glycol, sorbitol, and zinc chloride; Alcon Laboratories, Inc.), Purite (stabilized oxychloro complex; Allergan, Inc.)).

In some embodiments, the chemical entities described herein or a pharmaceutical composition thereof are suitable for local and topical administration to skin (e.g., ointments and creams). Ointments are semisolid preparations that are typically based on petrolatum or other petroleum derivatives. Creams containing the selected active agent are typically viscous liquid or semisolid emulsions, often either oil-in-water or water-in-oil. Cream bases are typically water-washable, and contain an oil phase, an emulsifier and an aqueous phase. The oil phase, also sometimes called the "internal" phase, is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation is generally a nonionic, anionic, cationic or amphoteric surfactant. As with other carriers or vehicles, an ointment base should be inert, stable, nonirritating and non-sensitizing.

For purposes of the disclosure, the amount or dose of the compounds, salts, solvates, or stereoisomers of any one the compounds of Formula (I), as set forth above, administered should be sufficient to effect, e.g., a therapeutic or prophylactic response, in the subject over a reasonable time frame. The dose will be determined by the efficacy of the particular compound and the condition of a human, as well as the body weight of a human to be treated.

It is understood by those of ordinary skill, that the compounds of the present disclosure are inhibitors of RNA polymerase I through one or more mechanisms of action. Without being limited to any particular theory, the compounds of the present disclosure can inhibit RNA Pol I by intercalation of the nucleic acids at G-C rich regions which block the polymerase activity.

One of ordinary skill in the art understands that p53 is a highly responsive molecule to cellular stress and DNA damage, and implicated in diverse diseases like cancer, ischemia, neuronal disorders, inflammation and also during physiological processes like in normal cellular metabolism, development and aging. Thus, the compounds of the present disclosure are useful in prevention or treatment of diseases involving the p53 pathways.

Therefore, in another aspect, the present disclosure provides the use of the compounds or the pharmaceutical compositions disclosed herein in an amount effective for activating upstream p53 pathways in a mammalian cell comprising contacting a cell or population of cells with a compound of Formula (I). Accordingly, in one aspect, provided herein is a method for activating upstream p53 pathways in a mammalian cell comprising contacting a cell or population of cells with a compound of Formula (I), a pharmaceutically acceptable salt thereof, or a pharmaceutical composition thereof. In certain embodiments, the step of contacting is carried out in vitro. In certain embodiments, the step of contacting is carried out in vivo.

In another aspect, the present disclosure provides the use of the compounds or the pharmaceutical compositions disclosed herein in an amount effective for modulating RNA Pol I activity in a mammalian cell comprising contacting a cell or population of cells with a compound of Formula (I). Accordingly, in one aspect, the disclosure provides a method for modulating RNA Pol I activity in a mammalian cell comprising contacting a cell or population of cells with a compound of Formula (I), a pharmaceutically acceptable salt thereof, or a pharmaceutical composition thereof. In certain embodiments, the step of contacting is carried out in vitro. In certain embodiments, the step of contacting is carried out in vivo.

This disclosure contemplates both monotherapy regimens as well as combination therapy regimens.

In some embodiments, the methods described herein can further include administering one or more additional therapies (e.g., one or more additional therapeutic agents and/or one or more therapeutic regimens) in combination with administration of the compounds described herein.

In certain embodiments, the methods described herein can further include administering one or more additional cancer therapies. In some embodiments, the one or more additional cancer therapies is chemotherapy, which can include administering one or more additional chemotherapeutic agents.

In another aspect, the present disclosure provides the use of the compounds or the pharmaceutical compositions disclosed herein in an amount effective for treating a condition, disease or disorder in which increased (e.g., excessive) Pol I activity contributes to the pathology and/or symptoms and/or progression of the condition, disease or disorder in a subject comprising administering to the subject a pharmaceutical composition comprising a compound of Formula (I). In some embodiments, the use comprises administering to the subject at least one additional therapeutic agent.

Accordingly, in one aspect, the present disclosure provides a method for treating a condition, disease or disorder in which increased (e.g., excessive) Pol I activity contributes to the pathology and/or symptoms and/or progression of the condition, disease or disorder in a subject comprising administering to the subject a compound of Formula (I), a pharmaceutically acceptable salt thereof, or a pharmaceutical composition thereof. In some embodiments, the method further comprises administering to the subject at least one additional therapeutic agent.

In some embodiments, the present disclosure provides the use of the compounds or the pharmaceutical compositions disclosed herein in an amount effective for treating cancer or a hyperproliferative disease in a subject comprising administering to the subject a pharmaceutical composition comprising a compound of Formula (I). In some embodiments, the use comprises administering to the subject at least one additional therapeutic agent.

Accordingly, in some embodiments, the disclosure provides a method for treating cancer or a hyperproliferative disease in a subject comprising administering to the subject a compound of Formula (I), a pharmaceutically acceptable salt thereof, or a pharmaceutical composition thereof. In certain of these embodiments, the method further comprises administering to the subject at least one additional therapeutic agent.

In some embodiments, the present disclosure provides the use of the compounds or the pharmaceutical compositions disclosed herein in an amount effective for an autoimmune disease or disorder in a subject comprising administering to the subject a pharmaceutical composition comprising a compound of Formula (I). In some embodiments, the use comprises administering to the subject at least one additional therapeutic agent.

Accordingly, in some embodiments, the disclosure provides a method for treating an autoimmune disease or disorder in a subject comprising administering to the subject a compound of Formula (I), a pharmaceutically acceptable salt thereof, or a pharmaceutical composition thereof. In certain of these embodiments, the method further comprises administering to the subject at least one additional therapeutic agent.

In some embodiments, the present disclosure provides the use of the compounds or the pharmaceutical compositions disclosed herein in an amount effective for the treatment of a condition associated with inflammation or pain in a subject comprising administering to the subject a pharmaceutical composition comprising a compound of Formula (I). In some embodiments, the use comprises administering to the subject at least one additional therapeutic agent.

Accordingly, in some embodiments, the disclosure provides a method for treating of a condition associated with inflammation or pain in a subject comprising administering to the subject a compound of Formula (I), a pharmaceutically acceptable salt thereof, or a pharmaceutical composition thereof. In certain of these embodiments, the method further comprises administering to the subject at least one additional therapeutic agent.

In another aspect, the present disclosure provides a method for modulating angiogenesis in a subject, comprising administering to the subject a compound of Formula (I), a pharmaceutically acceptable salt thereof, or a pharmaceutical composition thereof. In certain of these embodiments, the method further comprises administering to the subject at least one additional therapeutic agent.

The dose of the compounds, salts, solvates, or stereoisomers of any one the compounds of Formula (I), as set forth above, of the present disclosure also will be determined by the existence, nature and extent of any adverse side effects that might accompany the administration of a particular compound. Typically, an attending physician will decide the dosage of the compound with which to treat each individual patient, taking into consideration a variety of factors, such as age, body weight, general health, diet, sex, compound to be administered, route of administration, and the severity of the condition being treated. By way of example, and not intending to limit the disclosure, the dose of the compound can be about 0.001 to about 1000 mg/kg body weight of the subject being treated/day, from about 0.01 to about 100 mg/kg body weight/day, or from about 1 mg to about 100 mg/kg body weight/day. In some embodiments the dosage of the compound can be in the range of about 0.1 μM to about 100 μM, preferably about 1 μM to about 50 μM.

Alternatively, the compounds of the present disclosure can be modified into a depot form, such that the manner in which the compound is released into the body to which it is administered is controlled with respect to time and location within the body (see, for example, U.S. Pat. No. 4,450,150). Depot forms of compounds can be, for example, an implantable composition comprising the compound and a porous or non-porous material, such as a polymer, wherein the compound is encapsulated by or diffused throughout the material and/or degradation of the non-porous material. The depot is then implanted into the desired location within the body and the compounds are released from the implant at a predetermined rate.

In some embodiments, the compounds of the present disclosure provided herein can be controlled release compositions, i.e., compositions in which the one or more compounds are released over a period of time after administration. Controlled or sustained release compositions include formulation in lipophilic depots (e.g., fatty acids, waxes, oils). In another embodiment the composition is an immediate release composition, i.e., a composition in which all, or substantially all of the compound, is released immediately after administration.

In some embodiments, the compounds of the present disclosure can be delivered in a controlled release system. For example, the agent may be administered using intravenous infusion, an implantable osmotic pump, a transdermal patch, or other modes of administration. In an embodiment, a pump may be used. In some embodiments, polymeric materials can be used. In yet another embodiment, a controlled release system can be placed in proximity to the therapeutic target, i.e., the brain, thus requiring only a fraction of the systemic dose (see, e.g., *Design of Controlled Release Drug Delivery Systems*, Xiaoling Li and Bhaskara R. Jasti eds. (McGraw-Hill, 2006)).

The compounds included in the pharmaceutical compositions of the present disclosure may also include incorporation of the active ingredients into or onto particulate preparations of polymeric compounds such as polylactic acid, polyglycolic acid, hydrogels, etc., or onto liposomes, microemulsions, micelles, unilamellar or multilamellar vesicles, erythrocyte ghosts, or spheroplasts. Such compositions will influence the physical state, solubility, stability, rate of in vivo release, and rate of in vivo clearance.

In accordance with the present disclosure, the compounds of the present disclosure may be modified by, for example, the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline. The modified compounds are known to exhibit substantially longer half-lives in blood following intravenous injection, than do the corresponding unmodified compounds. Such modifications may also increase the compounds' solubility in aqueous solution, eliminate aggregation, enhance the physical and chemical stability of the compound, and greatly reduce the immunogenicity and reactivity of the compound. As a result, the desired in vivo biological activity may be achieved by the administration of such polymer-compound adducts less frequently, or in lower doses than with the unmodified compound.

An active agent and a therapeutic agent are used interchangeably herein to refer to a chemical or biological compound that induces a desired pharmacological and/or physiological effect, wherein the effect may be prophylactic or therapeutic. The terms also encompass pharmaceutically acceptable, pharmacologically active derivatives of those active agents specifically mentioned herein, including, but not limited to, salts, esters, amides, prodrugs, active metabolites, analogs and the like. When the terms "active agent," "pharmacologically active agent" and "drug" are used, then, it is to be understood that the disclosure includes the active agent per se as well as pharmaceutically acceptable, pharmacologically active salts, esters, amides, prodrugs, metabolites, analogs etc. The active agent can be a biological entity, such as a virus or cell, whether naturally occurring or manipulated, such as transformed.

The compounds of the present disclosure can optionally be employed in combination with one or more active agents selected from STING agonist compounds, anti-viral compounds, antigens, adjuvants, CTLA-4 and PD-1 pathway antagonists and other immunomodulatory agents, lipids, liposomes, peptides, anti-cancer agents, and chemotherapeutic agents including but not limited to PARP inhibitors, ACAT1 inhibiting compounds, autophagy inhibiting compounds, tyrosine kinase and signaling kinase inhibitors (such as AKT, MEK),), cell cycle inhibitors (such as CDK4/6, Wee 1, Plk, Aurora kinase), and chromatin modifiers.

Further examples of additional therapeutic agents include, without limitation, enzymes, receptor antagonists or agonists, hormones, growth factors, autogenous bone marrow, antibiotics, antimicrobial agents, RNA and DNA molecules and nucleic acids, and antibodies. Specific examples of useful therapeutic agents the above categories include: antineoplastics such as androgen inhibitors, antimetabolites, cytotoxic agents, and immunomodulators.

Additional therapeutic agents as used herein also include anti-cancer agents such as alkylating agents, nitrogen mustard alkylating agents, nitrosourea alkylating agents, antimetabolites, purine analog antimetabolites, pyrimidine analog antimetabolites, hormonal antineoplastics, natural antineoplastics, antibiotic natural antineoplastics, and vinca alkaloid natural antineoplastics.

Further examples of alkylating antineoplastic agents include carboplatin and cisplatin; nitrosourea alkylating antineoplastic agents, such as carmustine (BCNU); antimetabolite antineoplastic agents, such as methotrexate; pyrimidine analog antineoplastic agents, such as fluorouracil (5-FU) and gemcitabine; hormonal antineoplastics, such as goserelin, leuprolide, and tamoxifen; natural antineoplastics, such as aldesleukin, interleukin-2, docetaxel, etoposide, interferon; paclitaxel, other taxane derivatives, and tretinoin (ATRA); antibiotic natural antineoplastics, such as bleomycin, dactinomycin, daunorubicin, doxorubicin, and mitomycin; vinca alkaloid natural antineoplastics, such as vinblastine and vincristine, and PD1 inhibitors such as lambrolizumab.

As used herein, the term "subject" refers to any mammal, including, but not limited to, mammals of the order Rodentia, such as mice and hamsters, and mammals of the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simoids (monkeys) or of the order Anthropoids (humans and apes). An especially preferred mammal is the human.

As used herein, the term "modulate" means that the compounds of Formula (I), described herein either increase or decrease the activity of RNA Pol I.

As used herein, the term "hyperproliferative disease" includes cancer and other diseases such as neoplasias and hyperplasias. Cellular proliferative diseases include, for example, rheumatoid arthritis, inflammatory bowel disease, osteoarthritis, leiomyomas, adenomas, lipomas, hemangiomas, fibromas, vascular occlusion, restenosis, artherosclerosis, a pre-neoplastic lesion, carcinoma in situ, oral hairy leukoplakia, or psoriasis. In accordance with one or more embodiments, the term cancer can include any of acute lymphocytic cancer, acute myeloid leukemia, alveolar rhabdomyosarcomalung, cancer of the blood and heart (e.g., leukemia, lymphoma, carcinoma), cancer of the head and neck, skin cancer, blood and heart (e.g., leukemia, lymphoma, carcinoma), brain cancer, central nervous system cancer, peripheral nerve sheet tumors, breast cancer, cancer of the anus, anal canal, colorectum or anorectum, cancer of the eye, cancer of the intrahepatic bile duct, pancreatic cancer, cancer of the joints, cancer of the neck, gallbladder, or pleura, cancer of the nose, nasal cavity, or middle ear, cancer of the oral cavity, cancer of the vulva, cancer of the prostate, kidney cancer, chronic lymphocytic leukemia, chronic myeloid cancer, colon cancer, esophageal cancer, cervical cancer, breast cancer, gastrointestinal carcinoid tumor. Hodgkin lymphoma, hypopharynx cancer, kidney cancer, larynx cancer, liver cancer, lung cancer, malignant mesothelioma, melanoma, multiple myeloma, nasopharynx cancer, non-Hodgkin lymphoma, ovarian cancer, pancreatic cancer, peritoneum, omentum, and mesentery cancer, pharynx cancer, prostate cancer, rectal cancer, renal cancer (e.g., renal cell carcinoma (RCC)), small intestine cancer, soft tissue cancer, stomach cancer, testicular cancer, thyroid cancer, ureter cancer, and urinary bladder cancer.

As used herein, non-limiting examples of autoimmune diseases or disorders include: Acute Disseminated Encephalomyelitis (ADEM); Acute necrotizing hemorrhagic leukoencephalitis; Addison's disease; Agammaglobulinemia; Alopecia areata; Amyloidosis; Ankylosing spondylitis; Anti-GBM/Anti-TBM nephritis; Antiphospholipid syndrome (APS); Autoimmune angioedema; Autoimmune aplastic anemia; Autoimmune dysautonomia; Autoimmune hepatitis; Autoimmune hyperlipidemia; Autoimmune immunodeficiency; Autoimmune inner ear disease (AIED); Autoimmune myocarditis; Autoimmune pancreatitis; Autoimmune retinopathy; Autoimmune thrombocytopenic purpura (ATP); Autoimmune thyroid disease; Autoimmune urticaria; Axonal & neuronal neuropathies; Balo disease; Behcet's disease; Bullous pemphigoid; Cardiomyopathy; Castleman disease; Celiac disease; Chagas disease; Chronic inflammatory demyelinating polyneuropathy (CIDP); Chronic recurrent multifocal osteomyelitis (CRMO); Churg-Strauss syndrome; Cicatricial pemphigoid/benign mucosa pemphigoid; Crohn's disease; Cogans syndrome; Cold agglutinin disease; Congenital heart block; Coxsackie myocarditis; CREST disease; Essential mixed cryoglobulinemia; Demyelinating neuropathies; Dermatitis herpetiformis; Dermatomyositis; Devic's disease (neuromyelitis optica); Discoid lupus; Dressler's syndrome; Endometriosis; Eosinophilic fasciitis; Erythema nodosum; Experimental allergic encephalomyelitis; Evans syndrome; Fibrosing alveolitis; Giant cell arteritis (temporal arteritis); Glomerulonephritis; Goodpasture's syndrome; Granulomatosis with Polyangiitis (GPA) see Wegener's; Graves' disease; Guillain-Barre syndrome; Hashimoto's encephalitis; Hashimoto's thyroiditis; Hemolytic anemia; Henoch-Schonlein purpura; Herpes gestationis; Hypogammaglobulinemia; Idiopathic thrombocytopenic purpura (ITP); IgA nephropalothy; IgG4-related sclerosing disease; Immunoregulatory lipoproteins; Inclusion body myositis; Insulin-dependent diabetes (type 1); Interstitial cystitis; Juvenile arthritis; Juvenile diabetes; Kawasaki syndrome; Lambert-Eaton syndrome; Leukocytoclastic vasculitis; Lichen planus; Lichen sclerosus; Ligneous conjunctivitis; Linear IgA disease (LAD); Lupus (SLE); Lyme disease, chronic; Meniere's disease; Microscopic polyangiitis; Mixed connective tissue disease (MCTD); Mooren's ulcer; Mucha-Habermann disease; Multiple sclerosis; Myasthenia gravis; Myositis; Narcolepsy; Neuromyelitis optica (Devic's); Neutropenia; Ocularcicatricial pemphigoid; Optic neuritis; Palindromic rheumatism; PANDAS (Pediatric Autoimmune Neuropsychiatric Disorders Associated with *Streptococcus*); Paraneoplastic cerebellar degeneration; Paroxysmal nocturnal hemoglobinuria (PNH); Parry Romberg syndrome; Parsonnage-Turner syndrome; Pars planitis (peripheral uveitis); Pemphigus; Peripheral neuropathy; Perivenous encephalomyelitis; Pernicious anemia; POEMS syndrome; Polyarteritis nodosa; Type I, II, & III autoimmune polyglandular syndromes; Polymyalgia rheumatica; Polymyositis; Postmyocardial infarction syndrome; Postpericardiotomy syndrome; Progesterone dermatitis; Primary biliary cirrhosis; Primary sclerosing cholangitis; Psoriasis; Psoriatic arthritis; Idiopathic pulmonary fibrosis; Pyoderma gangrenosum; Pure red cell aplasia; Raynauds phenomenon; Reflex sympathetic dystrophy; Reiter's syndrome; Relapsing polychondritis; Restless legs syndrome; Retroperitoneal fibrosis; Rheumatic fever; Rheumatoid arthritis; Sarcoidosis; Schmidt syndrome; Scleritis; Scleroderma; Sjogren's syndrome; Sperm & testicular autoimmunity; Stiff person syndrome; Subacute bacterial endocarditis (SBE); Susac's syndrome; Sympathetic ophthalmia; Takayasu's arteritis; Temporal arteritis/Giant cell arteritis; Thrombocytopenic purpura (TTP); Tolosa-Hunt syndrome; Transverse myelitis; Ulcerative colitis; Undifferentiated connective tissue disease (UCTD); Uveitis; Vasculitis; Vesiculobullous dermatosis; Vitiligo; Wegener's granulomatosis (Granulo-matosis with Polyangiitis (GPA)).

As used herein, non-limiting examples of a conditions associated with inflammation or pain include: acid reflux, heartburn, acne, allergies and sensitivities, Alzheimer's disease, asthma, atherosclerosis, bronchitis, carditis, celiac disease, chronic pain, Crohn's disease, cirrhosis, colitis, dementia, dermatitis, diabetes, dry eyes, edema, emphysema, eczema, fibromyalgia, gastroenteritis, gingivitis, heart disease, hepatitis, high blood pressure, insulin resistance, interstitial cystitis, joint pain/arthritis/rheumatoid arthritis, metabolic syndrome (syndrome X), myositis, nephritis, obesity, osteopenia, osteoporosis, Parkinson's disease, periodontal disease, polyarteritis, polychondritis, psoriasis, scleroderma, sinusitis, Sjogren's syndrome, spastic colon, systemic candidiasis, tendonitis, urinary tract infections, vaginitis, inflammatory cancer (e.g., inflammatory breast cancer) and the like.

EXAMPLES

Exemplary compounds were prepared via several general synthetic routes set forth in the examples below. Any of the disclosed compounds of the present invention can be prepared according to one or more of these synthetic routes or specific examples, or via modifications thereof accessible to the person of ordinary skill in the art.

Chiral HPLC Method: A Chiralcel® OD (50×4.6 mm, 5 μm particle size) maintained at 40° C. was used. Analytes were resolved with an isocratic elution using 100% (acetonitrile+0.5% isopropyl alcohol) with a flow of 0.8 ml/min with a detection wavelength of 254 nm. Injection volume 5 μl at 0.5 mg/ml MeOH.

Exemplary compounds were prepared via several general synthetic routes set forth in the examples below. Any of the disclosed compounds of the present invention can be prepared according to one or more of these synthetic routes or specific examples, or via modifications thereof accessible to the person of ordinary skill in the art.

Intermediate 1

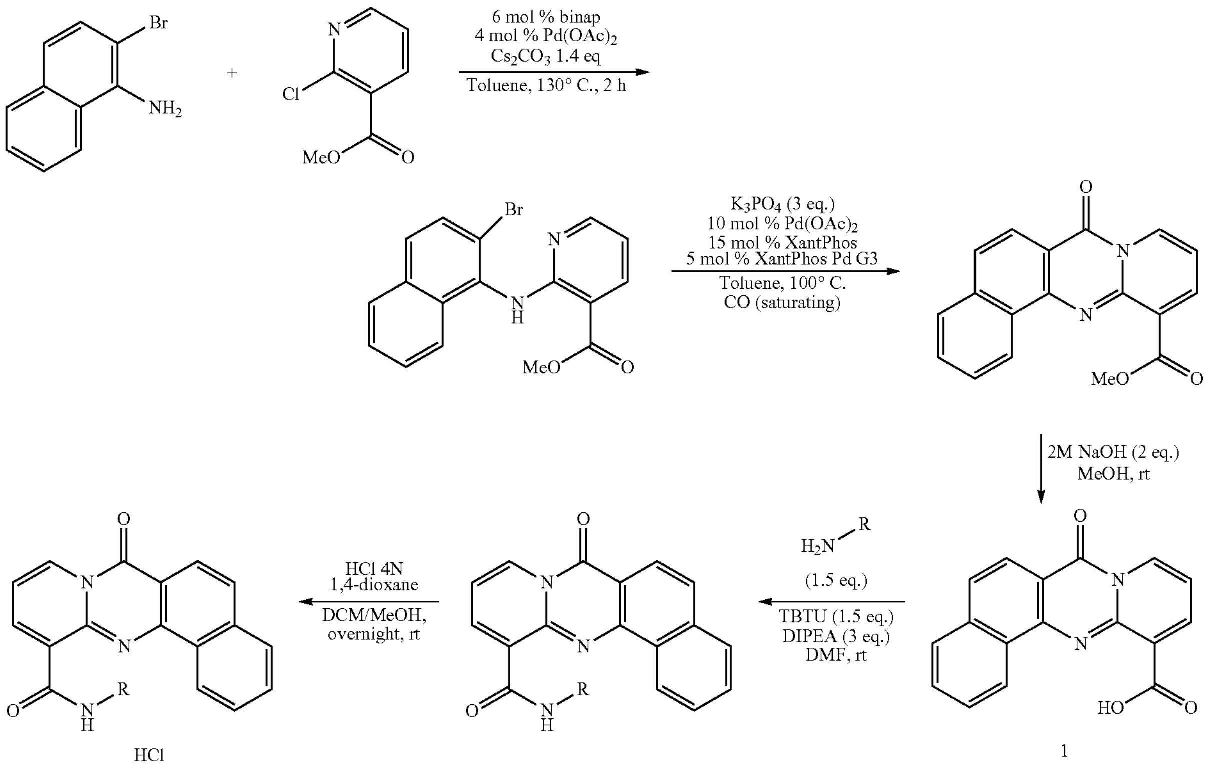

1

Intermediate 1: 7-oxo-7H-benzo[h]pyrido[2,1-b]quinazoline-12-carboxylic acid

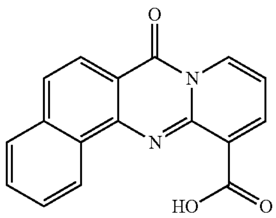 [SMILES: O=C(O)c1cccn2c(=O)c3ccc4ccccc4c3nc12]

Step 1: Preparation of methyl 2-((2-bromonaphthalen-1-yl)amino)nicotinate

In a 10-20 ml microwave vial with a magnetic stir bar, methyl 2-chloropyridine-3-carboxylate (98%, 1.00 g, 5.83 mmol) was dissolved in anhydrous Toluene (15 ml). The mixture was purged three times with Argon. Then 2-bromonaphthalen-1-amine (95%, 1499 mg, 6.41 mmol), diacetoxypalladium (53 mg, 0.233 mmol), [1-(2-diphenylphosphanyl-1-naphthyl)-2-naphthyl]-diphenyl-phosphane (218 mg, 0.350 mmol) and cesium carbonate (2659 mg, 8.16 mmol) were successively added. The mixture was purged again three times with Argon before the vial was sealed. The reaction was heated 2 h at 130° C. using microwave. Water was added and the mixture was extracted with ethyl acetate. Organic layers were combined, washed with brine, dried over sodium sulfate, filtrated and concentrated in vacuum. The crude material was washed with diethyl ether until purity>90% to afford the expected product methyl 2-((2-bromonaphthalen-1-yl)amino)nicotinate (810 mg, 34% Yield) as a grey solid. $^1$H NMR (400 MHz, DMSO-$d_6$) δ ppm 9.64 (s, 1H), 8.28 (dd, J=7.8, 1.9 Hz, 1H), 8.09 (dd, J=4.7, 1.9 Hz, 1H), 8.01 (d, J=7.7 Hz, 1H), 7.87 (d, J=8.8 Hz, 1H), 7.85-7.76 (m, 1H), 7.55 (m, 1H), 6.81 (dd, J=7.8, 4.7 Hz, 1H), 3.96 (s, 2H). MS [M+1]=359.

Step 2: Preparation of methyl 7-oxo-7H-benzo[h]pyrido[2,1-b]quinazoline-12-carboxylate In a 40 ml vial with a magnetic stir bar, was methyl 2-((2-bromonaphthalen-1-yl)amino)nicotinate (1.00 g, 2.80 mmol) in anhydrous Toluene (15 ml). The mixture was purged 3 times with argon then diacetoxypalladium (63 mg, 0.280 mmol), (5-diphenylphosphanyl-9,9-dimethyl-xanthen-4-yl)-diphenyl-phosphane (243 mg, 0.420 mmol), XantPhos Pd G3 (95%, 140 mg, 0.140 mmol) and tripotassium; phosphate (1808 mg, 8.40 mmol) were added. The mixture was purged again 3 times before adding hexakis (oxomethylidene)molybdenum (739 mg, 2.80 mmol). The vial was sealed and stirred at 115° C. overnight. The mixture was filtrated on Talc and rinsed with ethyl acetate. Resulting mixture was concentrated in vacuum. The crude material was purified via automated normal phase liquid chromatography on a 90 g SI60 15-40 μM column with Heptane to 75:25 ethyl acetate/heptane to afford methyl 7-oxo-7H-benzo[h]pyrido[2,1-b]quinazoline-12-carboxylate (310 mg, 30% Yield) as a yellow solid. $^1$H NMR (400 MHz, DMSO-$d_6$) δ ppm 9.08 (dd, J=7.3, 1.6 Hz, 2H), 9.00 (s, 1H), 8.24-8.15 (m, 3H), 8.09 (d, J=7.2 Hz, 2H), 7.94 (d, J=8.8 Hz, 2H), 7.90-7.76 (m, 4H), 7.69-7.58 (m, 1H), 7.41-7.24 (m, 4H), 4.05 (s, 5H), 1.65 (d, J=21.6 Hz, 1H). MS [M+1]=305.

Step 3: Preparation of 7-oxo-7H-benzo[h]pyrido[2,1-b]quinazoline-12-carboxylic acid In a 50 ml round-bottom flask charged with magnetic stir bar was dissolved methyl 11-oxo-12,18-diazatetracyclo [8.8.0.0^2,7.0^12,17]octadeca-1(10),2,4,6,8,13,15,17-octaene-16-carboxylate (310 mg, 1.02 mmol) in methanol (10 ml). A solution of 1 M sodium hydroxide (2.14 ml, 2.14 mmol) was added dropwise and the mixture was stirred overnight at room temperature. The mixture was acidified using HCl 1N until pH=2-3 then the product precipitated as a yellow solid. The solid was filtrated and dried in vacuum to obtain 7-oxo-7H-benzo[h]pyrido[2,1-b]quinazoline-12-carboxylic acid (250 mg, 84% Yield) as a yellow solid. $^1$H NMR (400 MHz, DMSO-$d_6$) δ ppm 16.81 (m, 1H), 9.22 (d, J=7.4 Hz, 1H), 8.75-8.65 (m, 2H), 8.28-8.15 (m, 2H), 8.03 (d, J=8.9 Hz, 1H), 7.92 (dd, J=6.1, 3.2 Hz, 2H), 7.45 (t, J=7.1 Hz, 1H). MS [M+1]=291.

Alternate method for preparation of 7-oxo-7H-benzo[h]pyrido[2,1-b]quinazoline-12-carboxylic acid:

Step 1: Preparation of 2-bromonaphthalen-1-amine

To a 250 mL round-bottom flask charged with a magnetic stir bar was added 1-bromopyrrolidine-2,5-dione (6.21 g, 34.92 mmol) and dichloromethane (69.8 mL). The resulting mixture was cooled to −78° C. before adding tetrachlorozirconium (406.87 mg, 1.75 mmol) and naphthalen-1-amine (5.00 g, 34.92 mmol). The reaction mixture was stirred and the dry-ice bath was allowed to evaporate overnight. The reaction was quenched with the addition of a saturated solution of sodium hydrogen carbonate to pH ~8-9 and was stirred for 30 minutes at room temperature. The mixture was transferred to a separatory funnel and diluted with water. The layers were separated and the aqueous layer was extracted with dichloromethane (3×50 mL). Combined organic layers were washed 1× with brine, dried over magnesium sulfate, filtered, and concentrated in vacuo. Crude material was separated into two batches (for ease of loading onto the instrument), 2 g and 4.7 g. Both batches were purified via automated normal phase liquid chromatography using a 120 g silica cartridge with 6-50% ethyl acetate/heptane. Purified fractions were combined and concentrated in vacuo to afford 2-bromonapthalen-1-amine (4.39 g, 57% yield) as a pinkish-white fluffy solid. $^1$H NMR (400 MHz, DMSO-$d_6$) δ 8.23-8.15 (m, 1H), 7.81-7.74 (m, 1H), 7.50-7.41 (m, 3H), 7.07 (d, 1H), 5.90 (s, 2H). MS [M+1]=222.

Step 2: Preparation of 2-Bromo-1-Iodo-Naphthalene

To a 40 mL vial charged with a magnetic stir bar was added water (3.9 mL), concentrated hydrogen chloride (1.17 mL, 13.96 mmol), and 2-bromonapthalen-1-amine (500 mg, 2.25 mmol). The resulting mixture was cooled to 0° C. After 10 minutes, a 0.7 M aqueous solution of sodium nitrite (186.42 mg, 2.70 mmol) was added. The resulting mixture was stirred at 0° C. until all solid dissolved before dropwise addition of a 4M aqueous solution of potassium iodide (454.06 mg, 3.38 mmol). After addition was complete, the ice bath was removed. The vial was allowed to warm to room temperature and was stirred at room temperature for 45 minutes then heated at 70° C. overnight. The reaction mixture was cooled to RT, quenched with 5 mL of 1M disodium dioxido-oxo-sulfanylidene-$\lambda^6$-sulfane, and stirred for 30 minutes at room temperature. The mixture was diluted with dichloromethane and transferred to a separatory funnel. The layers were separated and the aqueous layer was extracted with dichloromethane (3×25 mL). Combined organic layers were washed 1× with brine, dried over magnesium sulfate, filtered, and concentrated in vacuo. Purified via automated normal phase liquid chromatography using a 24 g silica cartridge with 100% heptane to afford 2-bromo-1-iodo-napthalene (500 mg, 67% yield) as a yellow solid. $^1$H NMR (400 MHz, DMSO-$d_6$) δ 8.20-8.14 (m, 1H), 7.97-7.91 (m, 2H), 7.79 (d, J=8.7 Hz, 1H), 7.70-7.58 (m, 2H). MS [M+1]=334.

Step 3: Preparation of methyl 2-((2-bromonaphthalen-1-yl)amino)nicotinate

To a 30 mL microwave vial charged with a magnetic stir bar was added 2-bromo-1-iodo-napthalene (254.18 mg, 0.76 mmol), methyl 2-aminopyridine-3-carboxylate (115 mg, 0.76 mmol), palladium (2+) diacetate (8.48 mg, 0.04 mmol), (5-diphenylphosphanyl-9,9-dimethylxanthen-4-yl)-diphenylphosphane (21.87 mg, 0.04 mmol), and cesium carbonate (347.23 mg, 1.07 mmol). In a separate vial, nitrogen was bubbled through anisole for 10 minutes prior to addition. After addition of anisole (4.65 mL), the reaction mixture was bubbled with nitrogen for 5 minutes before sealing the vial with a Teflon cap and heating at 130° C. overnight. After 18 hours, the reaction vial was cooled to room temperature, recharged with palladium (2+) diacetate (8.48 mg, 0.04 mmol) and (5-diphenylphosphanyl-9,9-dimethylxanthen-4-yl)-diphenylphosphane (21.87 mg, 0.04 mmol), bubbled with nitrogen for 5 minutes, then sealed and heated at 130° C. for 4 days. The vial was cooled to room temperature, recharged with palladium (2+) diacetate (8.48 mg, 0.04 mmol) and (5-diphenylphosphanyl-9,9-dimethylxanthen-4-yl)-diphenylphosphane (21.87 mg, 0.04 mmol), bubbled with nitrogen for 5 minutes, then sealed and heated at 130° C. for 24 hours. The reaction was cooled to room temperature and diluted with water. The aqueous layer was extracted with ethyl acetate (3×25 mL). Combined organic layers were washed 1× with brine, dried over magnesium sulfate, and concentrated in vacuo. Purified via automated normal phase liquid chromatography using a 12 g silica cartridge with 6-50% ethyl acetate/heptane to afford methyl 2-((2-bromonaphthalen-1-yl)amino)nicotinate (90 mg, 33% yield) as a white solid. $^{1}H$ NMR (400 MHz, DMSO-$d_6$) δ 9.64 (s, 1H), 8.33-8.22 (m, 1H), 8.13-8.05 (m, 2H), 8.04-7.97 (m, 1H), 7.87 (d, J=8.8 Hz, 1H), 7.84-7.76 (m, 1H), 7.60-7.48 (m, 2H), 6.80 (dd, J=7.8, 4.7 Hz, 1H), 3.95 (s, 3H). MS [M+1]=357.

Step 4: Preparation of methyl 7-oxo-7H-benzo[h]pyrido[2,1-b]quinazoline-12-carboxylate To a 5 mL microwave vial charged with a magnetic stir bar was added methyl 2-((2-bromonaphthalen-1-yl)amino) nicotinate (45 mg, 0.13 mmol), tripotassium phosphate (80.23 mg, 0.38 mmol), palladium (2+) diacetate (1.41 mg, 0.01 mmol), (5-diphenylphosphanyl-9,9-dimethylxanthen-4-yl)-diphenylphosphane (10.93 mg, 0.02 mmol), and (5-diphenylphosphanyl-9,9-dimethylxanthen-4-yl)-diphenylphosphane methanesulfonic acid palladium 2-phenylaniline (5.97 mg, 0.01 mmol). In a separate vial, toluene was saturated with carbon monoxide for 5 minutes prior to addition. After addition of toluene (2 mL), the reaction mixture was saturated with carbon monoxide for an additional 5 minutes before sealing the vial was a Teflon cap and heating at 100° C. for 2 days. The reaction mixture was cooled to room temperature, diluted with ethyl acetate, and poured into brine. The aqueous layer was extracted with additional ethyl acetate (3×25 mL). Combined organic layers were washed 1× with brine, dried over magnesium sulfate, filtered, and concentrated in vacuo to give 53.8 mg of a yellow-brown solid. This material was used without further purification. MS [M+1]=305.

Step 5: Preparation of 7-oxo-7H-benzo[h]pyrido[2,1-b]quinazoline-12-carboxylic acid To a 20 mL vial charged with a magnetic stir bar and containing methyl 7-oxo-7H-benzo[h]pyrido[2,1-b]quinazoline-12-carboxylate (50 mg, 0.16 mmol) was added methanol (1 mL) and 1M sodium hydroxide (0.16 mL, 0.33 mmol). The resulting mixture was stirred at room temperature overnight then concentrated in vacuo to give 64 mg of a yellow-brown solid. This material was used without further purification. MS [M+1]=291.

Example 1: N-[2-(dimethylamino)ethyl]-11-oxo-11H-5,10-diazatetraphene-6-carboxamide hydrochloride (Compound 101)

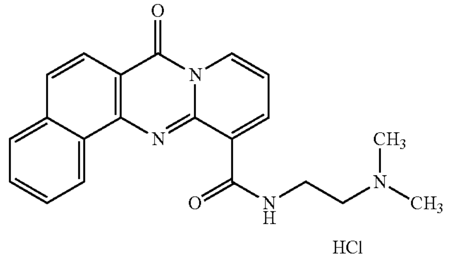 [SMILES: CN(C)CCNC(=O)c1cccn2c(=O)c3ccc4ccccc4c3nc12 ; Cl]

Method A: Synthesis of Amide Analogs with Commercially Available Amine

Preparation of N-(2-(dimethylamino)ethyl)-7-oxo-7H-benzo[h]pyrido[2,1-b]quinazoline-12-carboxamide

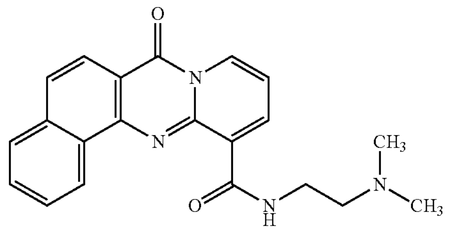 [SMILES: CN(C)CCNC(=O)c1cccn2c(=O)c3ccc4ccccc4c3nc12]

In a 10 ml vial with magnetic stir bar were added, 7-oxo-7H-benzo[h]pyrido[2,1-b]quinazoline-12-carboxylic acid (14 mg, 0.048 mmol), [benzotriazol-1-yloxy(dimethylamino)methylene]-dimethyl-ammonium; tetrafluoroborate (98%, 22 mg, 0.068 mmol) and N-ethyl-N-isopropyl-propan-2-amine (25.3 µl, 0.145 mmol) in DMF-Anhydrous. The resulting mixture was stirred 15 minutes at room temperature before adding N',N'-dimethylethane-1,2-diamine (7.40 µl, 0.068 mmol). The reaction mixture was stirred overnight at room temperature, then quenched with a saturated solution of sodium hydrogen carbonate, then the aqueous layer was extracted with Dichloromethane and ethyl acetate. The organic layers were combined, washed with brine, dried over sodium sulfate, filtrated and concentrated in vacuum to afford crude material as a yellow solid. The crude material was purified via automated normal phase liquid chromatography on a 12 g SI60 15-40 µM column with DCM 90/10 MeOH to afford N-(2-(dimethylamino)ethyl)-7-oxo-7H-benzo[h]pyrido[2,1-b]quinazoline-12-carboxamide (10 mg, 55% yield) as a yellow solid. $^{1}H$ NMR (400 MHz, DMSO-$d_6$) δ 10.67 (d, J=5.2 Hz, 1H), 9.18 (d, J=7.2 Hz, 1H), 9.10 (d, J=7.7 Hz, 1H), 8.74 (d, J=7.0 Hz, 1H), 8.22 (d, J=8.8 Hz, 1H), 8.12 (d, J=7.4 Hz, 1H), 7.96 (d, J=8.8 Hz, 1H), 7.86 (p, J=6.4 Hz, 2H), 7.37 (t, J=7.1 Hz, 1H), 3.70 (q, J=5.7 Hz, 2H), 2.62 (t, J=5.9 Hz, 2H), 2.32 (s, 6H). MS [M+1]=361.

Method B: Synthesis of Hydrochloride Analogs

To a 100 ml round bottom flask with a magnetic stir bar, N-(2-(dimethylamino)ethyl)-7-oxo-7H-benzo[h]pyrido[2,1- b]quinazoline-12-carboxamide (8.5 mg, 0.024 mmol) was dissolved in a DCM (1 ml)/MeOH (1 ml) mixture. A solution of 4 M 1,4-dioxane hydrochloride (18 μl, 0.071 mmol) was added dropwise and the reaction mixture was stirred 1 hour at room temperature. Diethyl ether was then added (50-100 ml) until precipitation of a yellow solid. The solid was filtrated and dried on vacuum overnight to afford N-(2-(dimethylamino)ethyl)-7-oxo-7H-benzo[h]pyrido[2,1-b]quinazoline-12-carboxamide; hydrochloride as a yellow solid. $^{1}$H NMR (400 MHz, DMSO-$d_6$) δ 10.66 (s, 1H), 10.10 (s, 1H), 9.19 (d, J=6.2 Hz, 1H), 8.84 (s, 1H), 8.61 (d, J=6.7 Hz, 1H), 8.23 (d, J=8.5 Hz, 1H), 8.14 (s, 1H), 7.98 (d, J=9.1 Hz, 1H), 7.90 (s, 2H), 7.39 (s, 1H), 4.04-3.98 (m, 2H), 2.90 (s, 6H). MS [M+1]=361

Examples 2-20 (infra) were synthesized according to Method A followed by Method B

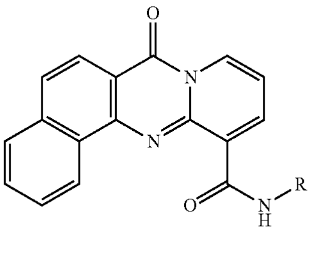

| Ex. | Name | R | Analytical Data | Preparation Information |
|---|---|---|---|---|
| 2 | (S)-N-(2-(3-hydroxypyrrolidin-1-yl)ethyl)-7-oxo-7H-benzo[h]pyrido[2,1-b]quinazoline-12-carboxamide; hydrochloride | 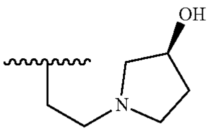 [SMILES: *CCN1CC[C@H](O)C1] | MS, ES$^+$ m/z, 403 (M + 1) $^{1}$H NMR (500 MHz, DMSO-$d_6$) δ 10.67 (dt, J = 11.1, 5.9 Hz, 1H), 9.19-9.13 (m, 1H), 8.82 (dd, J = 8.6, 4.3 Hz, 1H), 8.60 (ddd, J = 6.9, 4.3, 1.7 Hz, 1H), 8.21 (dd, J = 8.8, 3.4 Hz, 1H), 8.15-8.09 (m, 1H), 7.99-7.84 (m, 3H), 7.38 (td, J = 7.1, 4.0 Hz, 1H), 4.39 (dt, J = 4.9, 2.5 Hz, 1H), 3.99 (dt, J = 14.0, 6.4 Hz, 4H), 3.74 (dd, J = 11.1, 6.8 Hz, 1H), 3.70 (dd, J = 6.9, 5.0 Hz, 1H), 3.62-3.48 (m, 3H), 3.40-3.27 (m, 1H), 3.27-3.20 (m, 1H), 2.32-2.21 (m, 1H), 2.03-1.89 (m, 1H), 1.84 (dt, J = 14.2, 7.2 Hz, 1H) | Method A using (3S)-1-(2-aminoethyl)pyrrolidin-3-ol (139 μl, 1.013 mmol) and intermediate 1 (210 mg, 0.724 mmol) followed by Method B to give 145 mg (0.33 mmol, 89% yield) |
| 3 | (R)-N-(2-(3-hydroxypyrrolidin-1-yl)ethyl)-7-oxo-7H-benzo[h]pyrido[2,1-b]quinazoline-12-carboxamide; hydrochloride | 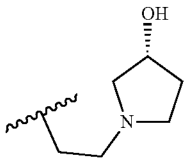 [SMILES: *CCN1CC[C@@H](O)C1] | MS, ES$^+$ m/z, 403 (M + 1) $^{1}$H NMR (500 MHz, DMSO-$d_6$) δ 10.67 (q, J = 6.0 Hz, 2H), 9.17 (ddd, J = 7.2, 3.7, 1.7 Hz, 2H), 8.82 (dd, J = 8.5, 4.3 Hz, 2H), 8.61 (ddd, J = 6.8, 4.9, 1.7 Hz, 2H), 8.22 (dd, J = 8.8, 2.9 Hz, 2H), 8.16-8.10 (m, 2H), 7.97 (dd, J = 8.8, 3.0 Hz, 2H), 7.95-7.85 (m, 4H), 7.38 (td, J = 7.1, 3.4 Hz, 2H), 4.45 (s, 1H), 4.40 (dt, J = 4.9, 2.4 Hz, 1H), 4.04-3.95 (m, 4H), 3.78-3.67 (m, 12H), 3.55 (ddd, J = 24.2, 12.4, 6.3 Hz, 17H), 3.42-3.20 (m, 4H), 2.30-2.21 (m, 1H), 2.02-1.92 (m, 2H), 1.83 (dd, J = 13.8, 6.4 Hz, 1H) | Method A using (3R)-1-(2-aminoethyl)pyrrolidin-3-ol (139 μl, 1.013 mmol) and intermediate 1 (210 mg, 0.724 mmol) followed by Method B to give 65 mg (0.15 mmol, 75% yield) |
| 4 | 7-oxo-N-(2-(pyrrolidin-1-yl)ethyl)-7H-benzo[h]pyrido[2,1-b]quinazoline-12-carboxamide hydrochloride | 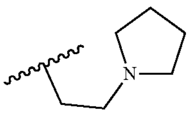 [SMILES: *CCN1CCCC1] | MS, ES$^+$ m/z, 387 (M + 1) $^{1}$H NMR (500 MHz, DMSO-$d_6$) δ 10.67 (t, J = 5.9 Hz, 1H), 9.17 (dd, J = 7.2, 1.7 Hz, 1H), 8.83 (d, J = 8.0 Hz, 1H), 8.60 (dd, J = 7.0, 1.7 Hz, 1H, 8.21 (d, J = 8.8 Hz, 1H), 8.15-8.10 (m, 1H), 7.99-7.85 (m, 3H), 7.38 (t, J = 7.1 Hz, 1H), 3.99 (q, J = 6.3 Hz, 2H), 3.64 (s, 2H), 3.50 (s, 2H), 3.11 (s, 2H), 2.05-1.79 (m, 4H). | Method A using N-(2-aminoethyl)pyrrolidine (22 μl, 0.170 mmol) and intermediate 1 (50 mg, 0.121 mmol) followed by Method B to give 82 mg (0.19 mmol, 84% yield) |
| 5 | N-(2-(4-hydroxypiperidin-1-yl)ethyl)-7-oxo-7H-benzo[h]pyrido[2,1-b]quinazoline-12-carboxamide hydrochloride | 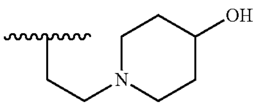 [SMILES: *CCN1CCC(O)CC1] | MS, ES$^+$ m/z, 417 (M + 1) $^{1}$H NMR (500 MHz, DMSO-d6) δ 10.65 (q, J = 5.8 Hz, 1H), 10.07 (s, 1H), 9.18 (dd, J = 7.2, 1.6 Hz, 1H), 8.87-8.81 (m, 1H), 8.60 (ddd, J = 7.1, 5.6, 1.7 Hz, 1H), 8.22 (d, J = 8.8 Hz, 1H), 8.16-8.11 (m, 1H), 7.98 (d, J = 8.8 Hz, 1H), 7.95-7.86 (m, 2H), 7.38 (t, J = 7.1 Hz, 1H), 4.02 (dt, J = 12.9, 6.4 Hz, 2H), 3.27 (q, J = 9.8 Hz, 2H), 3.14-3.04 (m, 1H), 1.96 (d, J = 13.0 Hz, 2H), 1.75 (d, J = 15.3 Hz, 1H), 1.67 (d, J = 13.2 Hz, 1H), 1.09 (t, J = 7.0 Hz, 1H). | Method A using 1-(2-aminoethyl)piperidin-4-ol (22 μl, 0.116 mmol) and intermediate 1 (30 mg, 0.083 mmol) followed by Method B to give 13 mg (0.029 mmol, 91% yield) |
| 6 | N-(2-(dimethylamino)-2-methylpropyl)-7-oxo-7H-benzo[h]pyrido[2,1-b]quinazoline-12-carboxamide hydrochloride | 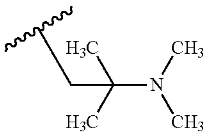 | MS, ES$^+$ m/z, 390 (M + 1) $^{1}$H NMR (500 MHz, DMSO-d6) δ 10.95 (t, J = 6.0 Hz, 1H), 9.86 (s, 1H), 9.20 (d, J = 7.1 Hz, 1H), 8.85 (d, J = 7.9 Hz, 1H), 8.67 (d, J = 7.0 Hz, 1H), 8.24 (d, J = 8.8 Hz, 1H), 8.14 (d, J = 7.7 Hz, 1H), 7.99 (d, J = 8.8 Hz, 1H), 7.93-7.83 (m, 2H), 7.40 (t, J = 7.1 Hz, 1H), 4.04 (d, J = 6.7 Hz, 2H), 2.80 (d, J = 4.9 Hz, 6H), 1.46 (s, 6H). | Method A using N,N,2-trimethylpropane-1,2-diamine (9.8 μl, 0.068 mmol) and intermediate 1 (20 mg, 0.048 mmol) followed by Method B to give 8.7 mg (0.021 mmol, 52% yield) |

-continued

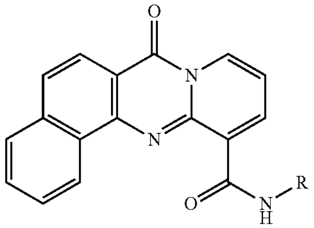

| Ex. | Name | R | Analytical Data | Preparation Information |
|---|---|---|---|---|
| 7 | N-(2-((3R,4R)-3,4-dihydroxy-pyrrolidin-1-yl)ethyl)-7-oxo-7H-benzo[h]pyrido[2,1-b]quinazoline-12-carboxamide hydrochloride | 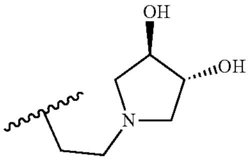 [SMILES: *CCN1C[C@@H](O)[C@H](O)C1] | MS, ES$^+$ m/z, 419 (M + 1) $^1$H NMR (500 MHz, DMSO-d6) δ 10.67 (t, J = 5.9 Hz, 1H), 10.30 (s, 1H), 9.19 (dd, J = 7.2, 1.7 Hz, 1H), 8.86-8.81 (m, 1H), 88.61 (dd, J = 7.0, 1.7 Hz, 1H), 8.23 (d, J = 8.8 Hz, 1H), 8.17-8.12 (m, 1H), 7.99 (d, J = 8.8 Hz, 1H), 7.93-7.85 (m, 2H), 7.39 (t, J = 7.1 Hz, 1H), 5.75 (s, 1H), 4.14 (d, J = 18.0 Hz, 2H), 3.99 (p, J = 6.7 Hz, 2H), 3.85-3.77 (m, 1H), 3.63-3.52 (m, 8H), 3.20 (d, J = 9.4 Hz, 1H). | Method A using 1-(2-aminoethyl)pyrrolidine-3,4-diol; dihydrochloride (28 mg, 0.127 mmol) and intermediate 1 (29 mg, 0.091 mmol) followed by Method B to give 7 mg (0.015 mmol, 46% yield) |
| 8 | N-(azetidin-3-yl)-7-oxo-7H-benzo[h]pyrido[2,1-b]quinazoline-12-carboxamide dihydrochloride | 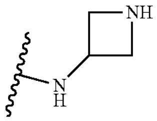 | MS, ES$^+$ m/z, 345 (M + 1) $^1$H NMR (500 MHz, DMSO-$d_6$) δ 10.76 (d, J = 6.5 Hz, 2H), 9.17 (dd, J = 7.2, 1.7 Hz, 2H), 8.86-8.81 (m, 2H), 8.54 (dd, J = 7.0, 1.6 Hz, 2H), 8.22 (d, J = 8.8 Hz, 2H), 8.17-8.11 (m, 2H), 7.98 (d, J = 8.9 Hz, 2H), 7.94-7.86 (m, 4H), 7.38 (t, J = 7.1 Hz, 2H), 5.75 (s, 1H), 5.04 (h, J = 7.8 Hz, 2H), 4.38 (s, 4H), 4.27 (d, J = 7.1 Hz, 3H). | Method A using tert-butyl 3-aminoazetidine-1-carboxylate (56 µl, 0.355 mmol) and intermediate 1 (40 mg, 0.119 mmol) followed by Method B to give 35 mg (0.082 mmol, 77% yield) |
| 9 | N-(1-methylazetidin-3-yl)-7-oxo-7H-benzo[h]pyrido[2,1-b]quinazoline-12-carboxamide hydrochloride | 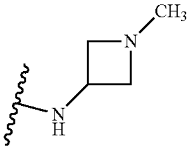 [SMILES: *NC1CN(C)C1] | MS, ES$^+$ m/z, 359 (M + 1) $^1$H NMR (500 MHz, DMSO-d6) δ 10.76 (s, 1H), 9.90 (s, 1H), 9.19 (dd, J = 7.2, 1.6 Hz, 2H), 8.86 (d, J = 7.9 Hz, 2H), 8.56 (d, J = 6.1 Hz, 2H), 8.24 (d, J = 8.8 Hz, 2H), 8.15 (d, J = 7.7 Hz, 2H), 7.99 (d, J = 8.8 Hz, 2H), 7.947.83 (m, 4H), 7.39 (t, J = 7.1 Hz, 2H), 2.96 (s, 6H), 2.54 (s, 1H). | Method A Using 1-methylazetidin-3-amine (13 µl, 0.145 mmol) and intermediate 1 (43 mg, 0.103 mmol) followed by Method B to give 8.6 mg (0.022 mmol, 78% yield) |
| 10 | (S)-N-(2-(dimethylamino) propyl)-7-oxo-7H-benzo[h]pyrido[2,1-b]quinazoline-12-carboxamide; hydrochloride | 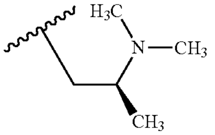 | MS, ES$^+$ m/z, 375 (M + 1) $^1$H NMR (600 MHz, DMSO-$d_6$) δ 10.67 (t, J = 6.1 Hz, 1H), 10.34 (s, 1H), 9.17 (dd, J = 7.1, 1.7 Hz, 1H), 8.86-8.80 (m, 1H), 8.59 (dd, J = 7.0, 1.7 Hz, 1H), 8.22 (d, J = 8.8 Hz, 1H), 8.16-8.11 (m, 1H), 7.99 (d, J = 8.8 Hz, 1H), 7.93-7.86 (m, 2H), 7.38 (t, J = 7.0 Hz, 1H), 4.06 (dt, J = 14.0.5.8 Hz, 1H), 3.88 (dt, J = 13.9, 6.6 Hz, 1H), 3.67 (ddt, J = 9.8, 6.7, 3.2 Hz, 1H), 2.83 (dd, J = 11.3, 5.0 Hz, 6H), 1.41 (d, J = 6.7 Hz, 3H). | Method A Using N,N-dimethylpropane-1,2-diamine (52 mg, 0.482 mmol) and intermediate 1 (100 mg, 0.344 mmol) (chiral separation) followed by Method B to give 53 mg (0.130 mmol, 90% yield on hydrochloride step only) |
| 11 | (R)-N-(2-(dimethylamino) propyl)-7-oxo-7H-benzo[h]pyrido[2,1-b]quinazoline-12-carboxamide; hydrochloride | 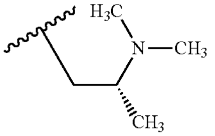 | MS, ES$^+$ m/z, 375 (M + 1) $^1$H NMR (600 MHz, DMSO-$d_6$) δ 10.68 (t, J = 6.2 Hz, 1H), 10.27 (s, 1H), 9.18 (dd, J = 7.1, 1.7 Hz, 1H), 8.86-8.81 (m, 1H), 8.59 (dd, J = 7.0, 1.7 Hz, 1H), 8.22 (d, J = 8.8 Hz, 1H), 8.16-8.10 (m, 1H), 7.97 (d, J = 8.7 Hz, 1H), 7.93-7.86 (m, 2H), 7.38 (t, J = 7.1 Hz, 1H), 4.09-4.02 (m, 4H), 3.88 (dt, J = 13.9, 6.6 Hz, 1H), 3.68 (ddt, J = 9.8, 6.7, 3.1 Hz, 1H), 2.83 (dd, J = 11.9, 5.0 Hz, 6H), 1.41 (d, J = 6.7 Hz, 3H). | Method A Using N,N-dimethylpropane-1,2-diamine (52 mg, 0.482 mmol) and intermediate 1 (100 mg, 0.344 mmol) (chiral separation) followed by Method B to give 49.7 mg (0.121 mmol, 73% yield on hydrochloride step only) |
| 12 | N-(2-(diethylamino) ethyl)-7-oxo-7H-benzo[h]pyrido[2,1-b]quinazoline-12-carboxamide; hydrochloride | 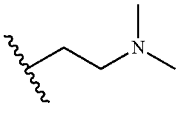 [SMILES: *CCN(C)C] | MS, ES$^+$ m/z, 389 (M + 1) $^1$H NMR (500 MHz, DMSO-$d_6$) δ 10.60 (t, J = 5.9 Hz, 1H), 10.12 (s, 1H), 9.18 (dd, J = 7.2, 1.6 Hz, 1H), 8.88-8.83 (m, 1H), 8.58 (dd, J = 7.0, 1.6 Hz, 1H), 8.23 (d, J = 8.8 Hz, 1H), 8.16-8.11 (m, 1H), 7.98 (d, J = 8.8 Hz, 1H), 7.93-7.86 (m, 2H), 7.38 (t, J = 7.1 Hz, 1H), 4.00 (q, J = 6.5 Hz, 2H), 3.41 (dq, J = 14.1, 6.9 Hz, 2H), 3.33-3.21 (m, 4H), 1.27 (t, J = 7.3 Hz, 6H). | Method A Using N,N-diethylethylenediamine (22 mg, 0.193 mmol) and intermediate 1 (40 mg, 0.138 mmol) followed by Method B to give 26 mg (0.059 mmol, 88% yield) |
| 13 | (S)-N-(1-(dimethylamino) propan-2-yl)-7-oxo-7H-benzo[h]pyrido[2,1-b]quinazoline-12-carboxamide; hydrochloride | 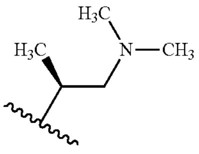 [SMILES: *[C@@H](C)CN(C)C] | MS, ES$^+$ m/z, 375 (M + 1) $^1$H NMR (500 MHz, DMSO-$d_6$) δ 10.45 d, J = 8.5 Hz, 1H), 9.49 (s, 1H), 9.19 (d, J = 6.1 Hz, 1H), 8.83 (d, J = 7.2 Hz, 1H), 8.63 (d, J = 6.0 Hz, 1H), 8.23 (d, J = 8.8 Hz, 1H), 8.15 (d, J = 6.9 Hz, 1H), 7.99 (d, J = 8.8 Hz, 1H), 7.89 (s, 2H), 7.40 (t, J = 7.1 Hz, 1H), 4.73 (s, 1H), 3.63 (s, 8H), 3.44 (t, J = 9.4 Hz, 1H), 2.93 (d, J = 4.6 Hz, 3H), 2.84 (d, J = 4.6 Hz, 3H), 1.54 (d, J = 6.5 Hz, 3H). | Method A Using (2S)-2-aminopropyl]dimethylamine (15.5 mg, 0.145 mmol) and intermediate 1 (30 mg, 0.103 mmol) followed by Method B to give 16.5 mg (0.040 mmol, 47% yield) |

-continued

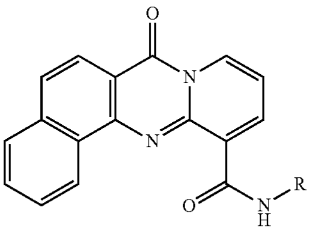

| Ex. | Name | R | Analytical Data | Preparation Information |
|---|---|---|---|---|
| 14 | (R)-N-(1-(dimethylamino)propan-2-yl)-7-oxo-7H-benzo[h]pyrido[2,1-b]quinazoline-12-carboxamide; hydrochloride | 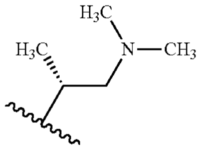 | MS, $ES^+$ m/z, 375 (M + 1) $^1H$ NMR (600 MHz, DMSO-$d_6$) δ 10.45 (d, J = 8.6 Hz, 1H), 9.49 (s, 1H), 9.19 (dd, J = 7.1, 1.7 Hz, 1H), 8.85-8.81 (m, 1H), 8.63 (dd, J = 7.0, 1.7 Hz, 1H), 8.23 (d, J = 8.8 Hz, 1H), 8.17-8.13 (m, 1H), 7.99 (d, J = 8.8 Hz, 1H), 7.93-7.85 (m, 2H), 7.40 (t, J = 7.1 Hz, 1H), 4.76-4.68 (m, 1H), 3.69 (s, 10H), 3.47-3.32 (m, 3H), 2.93 (d, J = 4.9 Hz, 3H), 2.83 (d, J = 4.8 Hz, 3H), 1.54 (d, J = 6.7 Hz, 3H), 1.09 (t, J = 7.0 Hz, 1H) | Method A Using (2R)-N1,N1-dimethylpropane-1,2-diamine (15 mg, 0.145 mmol) and intermediate 1 (30 mg, 0.103 mmol) followed by Method B to give 5 mg (0.012 mmol, 15% yield) |
| 15 | 7-oxo-N-(2-(piperidin-1-yl)ethyl)-7H-benzo[h]pyrido[2,1-b]quinazoline-12-carboxamide; hydrochloride | 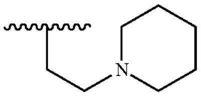 [SMILES: *CCN1CCCCC1] | MS, $ES^+$ m/z, 401 (M + 1) $^1H$ NMR (500 MHz, DMSO-$d_6$) δ 10.65 (t, J = 5.9 Hz, 1H), 9.19 (dd, J = 7.2, 1.7 Hz, 1H), 8.87-8.82 (m, 1H), 8.60 (dd, J = 7.0, 1.7 Hz, 1H), 8.23 (d, J = 8.8 Hz, 1H), 8.17-8.11 (m, 1H), 8.05-7.96 (m, 1H), 7.94-7.86 (m, 2H), 7.39 (t, J = 7.1 Hz, 1H), 4.02 (q, J = 6.4 Hz, 2H), 3.61 (d, J = 11.7 Hz, 2H), 3.42 (q, J = 6.5 Hz, 2H), 3.03 (q, J = 8.9 Hz, 2H), 1.83 (d, J = 14.3 Hz, 2H), 1.70 (d, J = 12.6 Hz, 2H). | Method A Using 2-(1-piperidyl)ethanamine (25 mg, 0.193 mmol) and intermediate 1 (40 mg, 0.134 mmol) followed by Method B to give 18 mg (0.038 mmol, 73% yield) |
| 16 | N-(2-(methylamino)ethyl)-7-oxo-7H-benzo[h]pyrido[2,1-b]quinazoline-12-carboxamide hydrochloride | 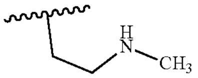 [SMILES: *CCNC] | MS, $ES^+$ m/z, 347 (M + 1) $^1H$ NMR (500 MHz, DMSO-d) δ 10.70 (t, J = 5.9 Hz, 1H), 9.18 (dd, J = 7.2, 1.7 Hz, 1H), 8.86 (s, 2H), 8.82-8.78 (m, 1H), 8.63 (dd, J = 7.0, 1.7 Hz, 1H), 8.22 (d, J = 8.8 Hz, 1H), 8.15.8.09 (m, 1H), 7.97 (d, J = 8.8 Hz, 1H), 7.93-7.85 (m, 2H), 7.39 (t, J = 7.1 Hz, 1H), 3.92 (q, J = 6.2 Hz, 2H), 3.30-3.24 (m, 2H), 2.64 (t, J = 5.0 Hz, 3H). | Method A Using tert-butyl (2-aminoethyl)methylcarbamate (14 mg, 0.193 mmol) and intermediate 1 (40 mg, 0.134 mmol) followed by Method B to give 9.3 mg (0.024 mmol, 36% yield) |
| 17 | N-(2-aminoethyl)-7-oxo-7H-benzo[h]pyrido[2,1-b]quinazoline-12-carboxamide hydrochloride | 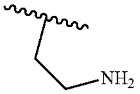 [SMILES: *CCN] | MS, $ES^+$ m/z, 333 (M + 1) $^1H$ NMR (500 MHz, DMSO-$d_6$) δ 10.64 (t, J = 5.8 Hz, 1H), 9.25-9.16 (m, 1H), 8.85-8.79 (m, 1H), 8.62 (dd, J = 7.0, 1.7 Hz, 1H), 8.27-8.21 (m, 1H), 8.15 (dd, J = 9.8, 8.2 Hz, 1H), 8.01 (dd, J = 21.4, 8.8 Hz, 3H), 7.94-7.84 (m, 2H), 7.39 (t, J = 7.1 Hz, 1H), 5.75 (s, 1H), 3.86 (d, J = 12.5 Hz, 7H), 3.17 (s, 3H) | Method A Using tert-butyl N-(2-aminoethyl)carbamate (31.5 mg, 0.193 mmol) and intermediate 1 (40 mg, 0.134 mmol) followed by Method B to give 20 mg (0.050 mmol, quant.) |
| 18 | N-(2-(ethyl(methyl)amino)ethyl)-7-oxo-7H-benzo[h]pyrido[2,1-b]quinazoline-12-carboxamide hydrochloride | 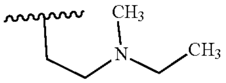 [SMILES: *CCN(C)CC] | MS, $ES^+$ m/z, 375 (M + 1) $^1H$ NMR (500 MHz, DMSO-$d_6$) δ 10.63 (t, J = 5.9 Hz, 1H), 9.89 (s, 1H), 9.18 (dd, J = 7.2, 1.7 Hz, 1H), 8.84 (dt, J = 7.1, 3.2 Hz, 1H), 8.60 (dd, J = 7.0, 1.7 Hz, 1H), 8.23 (d, J = 8.8 Hz, 1H), 8.14 (dt, J = 5.3, 3.1 Hz, 1H), 7.98 (d, J = 8.8 Hz, 1H), 7.93-7.86 (m, 2H), 7.39 (t, J = 7.1 Hz, 1H), 4.01 (q, J = 6.5 Hz, 2H), 3.43-3.27 (m, 3H), 3.25-3.14 (m, 1H), 2.88 (d, J = 5.0 Hz, 3H), 1.26 (t, J = 7.3 Hz, 3H). | Method A Using N-ethyl-N-methylethane-1,2-diamine (18 mg, 0.166 mmol) and intermediate 1 (40 mg, 0.118 mmol) followed by Method B to give 18 mg (0.043 mmol, 94% yield) |
| 19 | (S or R)-N-(2-(methylamino)propyl)-7-oxo-7H-benzo[h]pyrido[2,1-b]quinazoline-12-carboxamide; hydrochloride | 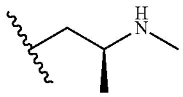 [SMILES: *C[C@H](C)NC] | MS, $ES^+$ m/z, 362 (M + 1) $[\alpha]_{20}$ = -38° (length: 10 cm, C = 1 mg/ml, Solvent: MeOH, Lamp (Na+) = 589 nm, Temperature: 20° C.) $^1H$ NMR (400 MHz, DMSO-d6) δ 10.76 (t, J = 5.9 Hz, 1H), 9.19 (dd, J = 7.2, 1.5 Hz, 1H), 9.06-8.91 (m, 1H), 8.91-8.78 (m, 2H), 8.63 (dd, J = 7.0, 1.5 Hz, 1H), 8.23 (d, J = 8.8 Hz, 1H), 8.19-8.09 (m, 1H), 7.98 (d, J = 8.8 Hz, 1H), 7.95-7.85 (m, 2H), 7.40 (t, J = 7.1 Hz, 1H), 3.92 (t, J = 5.9 Hz, 2H), 3.59-3.45 (m, 1H), 2.65 (t, J = 5.3 Hz, 3H), 1.39 (d, J = 6.6 Hz, 3H). | Method A Using tert-butyl N-(1-aminopropan-2-yl)-N-methylcarbamate (109 mg, 0.579 mmol) and intermediate 1 (120 mg, 0.413 mmol after chiral separation) followed by Method B to give 70 mg (0.175 mmol, quant.) |

-continued

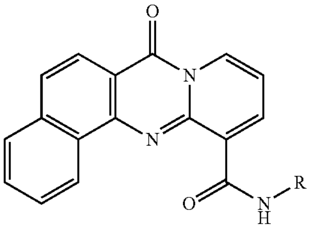

| Ex. | Name | R | Analytical Data | Preparation Information |
|---|---|---|---|---|
| 20 | (R or S)-N-(2-(methylamino) propyl)-7-oxo-7H-benzo[h]pyrido[2,1-b]quinazoline-12-carboxamide; hydrochloride | 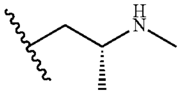 [SMILES: *C[C@@H](C)NC] | MS, $ES^+$ m/z, 362 (M + 1) $[\alpha]_{20}$ = +48° (length: 10 cm, C = 1 mg/ml, Solvent:MeOH, Lamp ($Na^+$) = 589 nm, Temperature: 20° C.) $^1$H NMR (400 MHz, DMSO-d6) δ 10.75 (t, J = 6.1 Hz, 1H), 9.18 (dd, J = 7.2, 1.6 Hz, 1H), 9.13-9.00 (m, 1H), 9.00-8.86 (m, 1H), 8.85-8.79 (m, 1H), 8.63 (dd, J = 7.0, 1.6 Hz, 1H), 8.22 (d, J = 8.8 Hz, 1H), 8.18-8.09 (m, 1H), 7.97 (d, J = 8.9 Hz, 1H), 7.94-7.85 (m, 2H), 7.39 (t, J = 7.1 Hz, 1H), 3.92 (t, J = 5.9 Hz, 2H), 3.60-3.44 (m, 1H), 2.64 (t, J = 5.4 Hz, 3H), 1.40 (d, J = 6.6 Hz, 3H). | Method A Using tert-butyl N-(1-aminopropan-2-yl)-N-methylcarbamate (109 mg, 0.579 mmol) and intermediate 1 (120 mg 0.413 mmol after chiral separation) followed by Method B to give 68 mg (0.171 mmol, 99%) |

Method C: Synthesis of Amines

Preparation of 2-(3,3-dimethylpyrrolidin-1-yl)ethan-1-amine hydrochloride

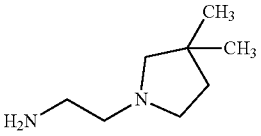

HCl

In a 50 ml flask, tert-butyl (2-bromoethyl)carbamate (95%, 202 mg, 0.86 mmol) was dissolved in Acetonitrile (4 mL). 3,3-dimethylpyrrolidine hydrochloride (1:1) (97%, 100 mg, 0.715 mmol) and N-ethyl-N-isopropyl-propan-2-amine (88 μL, 2.15 mmol) were added and the reaction mixture was stirred overnight at rt. The reaction mixture was diluted with DCM and the aqueous layer was extracted with DCM. Combined organic layers were washed with $H_2O$ and brine, dried over $Na_2SO_4$ and solvent were removed under vacuum. Tert-butyl N-[2-(3,3-dimethylpyrrolidin-1-yl) ethyl]carbamate (61 mg, 0.251 mmol) was dissolved in 1,4-Dioxane (2 mL). A 4 M hydrogen chloride (627 μL, 2.51 mmol) solution in dioxane was added and the resulting mixture was stirred at rt overnight. Solvent was evaporated under vacuum to afford 2-(3,3-dimethylpyrrolidin-1-yl) ethanamine; hydrochloride (57.5 mg, 100% Yield) as a pale pink solid. Crude material was used without further purification in the coupling step.

Examples 21-40 (infra) were synthesized according to Method A, with commercially available amines or amines prepared according to Method C, followed by Method B.

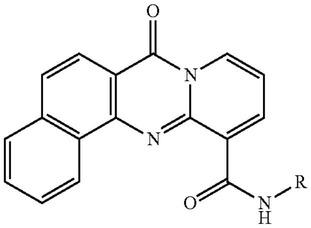

| Ex. | Name | R | Analytical Data | Preparation Information |
|---|---|---|---|---|
| 21 | N-(2-(3,3-dimethylpyrrolidin-1-yl)ethyl)-7-oxo-7H-benzo[h]pyrido[2,1-b]quinazoline-12-carboxamide hydrochloride | 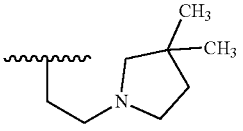 [SMILES: *CCN1CCC(C)(C)C1] | MS, $ES^+$ m/z, 415 (M + 1) 1H NMR (600 MHz, DMSO-d6) δ 10.69 (t, J = 5.9 Hz, 1H), 9.19 (dd, J = 7.1, 1.6 Hz, 1H), 8.84 (d, J = 9.1 Hz, 1H), 8.62 (dd, J = 7.0, 1.6 Hz, 1H), 8.24 (d, J = 8.8 Hz, 1H), 8.17-8.12 (m, 1H), 7.99 (d, J = 8.9 Hz, 1H), 7.93-7.87 (m, 2H), 7.40 (t, J = 7.0 Hz, 1H), 3.99-3.94 (m, 2H), 3.79-3.70 (m, 1H), 3.56 (s, 4H), 3.50 (dt, J = 11.4, 5.7 Hz, 2H), 3.40-3.35 (m, 8H), 3.03-2.96 (m, 1H), 1.93-1.86 (m, 1H), 1.74 (dt, J = 13.1, 7.9 Hz, 1H), 1.15 (s, 3H), 1.10-1.07 (m, 4H). | Method A using 2-(3,3-dimethylpyrrolidin-1-yl)ethanamine; hydrochloride (49 mg, 0.278 mmol) prepared according Method C and intermediate 1 (40 mg, 0.134 mmol) followed by Method B to give 1.7 mg (0.003 mmol, 11% yield) |

-continued

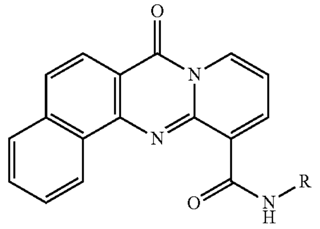

| Ex. | Name | R | Analytical Data | Preparation Information |
|---|---|---|---|---|
| 22 | 7-oxo-N-(2-(4-oxopiperidin-1-yl)ethyl)-7H-benzo[h]pyrido[2,1-b]quinazoline-12-carboxamide hydrochloride | 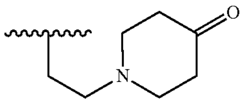 [SMILES: *CCN1CCC(=O)CC1] | MS, ES$^+$ m/z, 415 (M+1)) 1H NMR (600 MHz, DMSO-d6) δ 10.70 (t, J = 5.7 Hz, 6H), 10.12 (s, 4H), 9.20 (d, J = 6.0 Hz, 6H), 8.86 (s, 4H), 8.64 (s, 5H), 8.24 (d, J = 8.8 Hz, 7H), 8.15 (s, 3H), 8.14 (s, 4H), 7.99 (d, J = 8.4 Hz, 7H), 7.89 (s, 10H), 7.40 (t, J = 7.0 Hz, 8H), 4.06 (s, 6H), 3.90 (s, 5H), 3.77 (s, 2H), 3.60 (s, 9H), 3.16 (s, 10H), 2.77 (s, 4H), 1.23 (s, 4H), 0.85 (s, 1H). | Method A using 1-(2-aminoethyl)piperidin-4-one (61.7 mg, 0.434 mmol) prepared according Method C and intermediate 1 (100 mg, 0.310 mmol) followed by Method B to give 4.4 mg (0.001 mmol, 67% yield) |
| 23 | (S)-N-(2-(3-methoxypyrrolidin-1-yl)ethyl)-7-oxo-7H-benzo[h]pyrido[2,1-b]quinazoline-12-carboxamide hydrochloride | 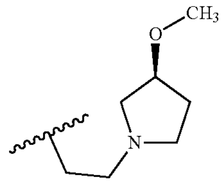 [SMILES: *CCN1CC[C@H](OC)C1] | MS, ES$^+$ m/z, 417 (M + 1) 1H NMR (600 MHz, DMSO-d6) δ 10.68 (s, 3H), 10.28 (s, 1H), 9.18 (d, J = 6.1 Hz, 2H), 8.83 (dd, J = 6.1, 3.0 Hz, 2H), 8.61 (d, J = 6.6 Hz, 2H), 8.22 (d, J = 8.8 Hz, 2H), 8.13 (dd, J = 6.1, 3.0 Hz, 2H), 7.97 (d, J = 8.8 Hz, 2H), 7.92-7.86 (m, 4H), 7.39 (t, J = 7.0 Hz, 2H), 4.12 (d, J = 28.3 Hz, 2H), 3.99 (d, J = 5.9 Hz, 3H), 3.75 (d, J = 49.1 Hz, 4H), 3.53 (s, 2H), 2.30 (s, 1H), 2.14 (s, 1H), 1.98 (S, 2H). | Method A using 2-[(3S)-3-methoxypyrrolidin-1-yl]ethanamine (74.7 mg, 0.413 mmol) prepared according Method C and intermediate 1 (50 mg, 0.138 mmol) followed by Method B to give 20 mg (0.044 mmol, 56% yield) |
| 24 | (R)-N-(2-(3-methoxypyrrolidin-1-yl)ethyl)-7-oxo-7H-benzo[h]pyrido[2,1-b]quinazoline-12-carboxamide hydrochloride | 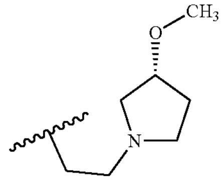 [SMILES: *CCN1CC[C@@H](OC)C1] | MS, ES$^+$ m/z, 417 (M + 1) 1H NMR (600 MHz, DMSO-d6) δ 10.68 (dt, J = 11.3, 6.1 Hz, 3H), 10.29 (s, 1H), 9.18 (dd, J = 5.2, 1.9 Hz, 2H), 8.85-8.80 (m, 2H), 8.61 (t, J = 5.8 Hz, 2H), 8.22 (d, J = 8.8 Hz, 2H), 8.13 (dd, J = 6.3, 2.8 Hz, 2H), 7.98 (d, J = 8.7 Hz, 2H), 7.90 (dt, J = 5.7, 3.5 Hz, 4H), 7.39 (td, J = 7.0, 3.1 Hz, 2H), 4.14 (s, 1H), 4.09 (s, 1H), 4.00-3.97 (m, 4H), 3.82-3.74 (m, 2H), 3.58-3.51 (m, 4H), 3.29-3.20 (m, 10H), 2.30 (td, J = 15.0, 6.1 Hz, 1H), 2.14 (dd, J = 13.5, 6.0 Hz, 1H), 1.99-1.94 (m, 2H). | Method A using 2-[(3R)-3-methoxypyrrolidin-1-yl]ethanamine (50 mg, 0.276 mmol) prepared according Method C and intermediate 1 (50 mg, 0.138 mmol) followed by Method B to give 9 mg (0.020 mmol, 33% yield) |
| 25 | (R)-N-(2-(3-fluoropyrrolidin-1-yl)ethyl)-7-oxo-7H-benzo[h]pyrido[2,1-b]quinazoline-12-carboxamide hydrochloride | 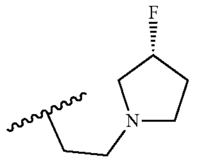 [SMILES: *CCN1CC[C@@H](F)C1] | MS, ES$^+$ m/z, 405 (M + 1) 1H NMR (600 MHz, DMSO-d6) δ 10.69 (d, J = 5.7 Hz, 1H), 10.46 (s, 1H), 9.19 (dd, J = 7.1, 1.7 Hz, 1H), 8.86-8.82 (m, 1H), 8.65-8.59 (m, 1H), 8.23 (d, J = 8.8 Hz, 1H), 8.14 (d, J = 7.0 Hz, 1H), 7.99 (d, J = 8.8 Hz, 1H), 7.93-7.86 (m, 2H), 7.40 (t, J = 7.0 Hz, 1H), 5.56-5.33 (m, 1H), 4.00 (p, J = 6.4 Hz, 2H), 3.88-3.73 (m, 1H), 3.63-3.57 (m, 2H). | Method A using 2-[(3R)-3-fluoropyrrolidin-1-yl]ethanamine; hydrochloride (75 mg, 0.444 mmol) prepared according Method C and intermediate 1 (50 mg, 0.148 mmol) followed by Method B to give 1 mg (0.002 mmol, 8% yield) |
| 26 | N-((S)-1-((3S,4S)-3,4-dihydroxy-pyrrolidin-1-yl)propan-2-yl)-7-oxo-7H-benzo[h]pyrido[2,1-b]quinazoline-12-carboxamide hydrochloride | 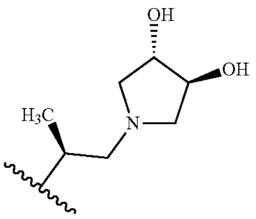 [SMILES: *[C@@H](C)CN1C[C@H](O)[C@@H](O)C1] | MS, ES$^+$ m/z, 433 (M + 1) $^1$H NMR (600 MHz, DMSO-$d_6$) δ 10.62 (d, J = 8.7 Hz, 1H), 9.94 (s, 1H), 9.20 (dd, J = 7.1, 1.7 Hz, 1H), 8.83-8.78 (m, 1H), 8.67 (dd, J = 7.0, 1.7 Hz, 1H), 8.23 (d, J = 8.8 Hz, 1H), 8.15 (dd, J = 7.1, 2.1 Hz, 1H), 7.99 (d, J = 8.8 Hz, 1H), 7.92-7.85 (m, 2H), 7.41 (t, J = 7.1 Hz, 1H), 4.72 (dp, J = 9.8, 3.4 Hz, 1H), 4.16 (d, J = 2.0 Hz, 1H), 4.10 (d, J = 4.2 Hz, 1H), 3.78 (ddd, J = 12.0, 7.2, 4.4 Hz, 1H), 3.67 (dd, J = 12.1, 5.6 Hz, 1H), 3.58 (ddd, J = 17.4, 10.5, 3.9 Hz, 5H), 3.47-3.36 (m, 4H), 3.18-3.10 (m, 1H), 1.54 (d, J = 6.8 Hz, 3H). | Method A using (3S,4S)-1-[(2S)-2-aminopropyl]pyrrolidine-3,4-diol; hydrochloride (81 mg, 0.413 mmol) prepared according Method C and intermediate 1 (40 mg, 0.138 mmol) followed by Method B to give 15 mg (0.032 mmol, 69% yield) |
| 27 | N-((R)-1-((3S,4S)-3,4-dihydroxy-pyrrolidin-1-yl)propan-2-yl)-7-oxo-7H-benzo[h]pyrido[2,1-b]quinazoline-12-carboxamide hydrochloride | 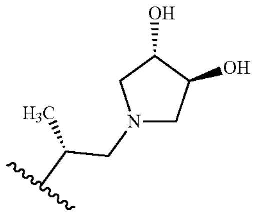 [SMILES: *[C@H](C)CN1C[C@H](O)[C@@H](O)C1] | MS, ES$^+$ m/z, 433 (M + 1) $^1$H NMR (500 MHz, DMSO-$d_6$) δ 10.52 (d, J = 8.2 Hz, 1H), 10.11 (s, 1H), 9.19 (dd, J = 7.1, 1.6 Hz, 1H), 8.85-8.80 (m, 1H), 8.62 (dd, J = 7.0, 1.7 Hz, 1H), 8.23 (d, J = 8.8 Hz, 1H), 8.18-8.12 (m, 1H), 7.99 (d, J = 8.9 Hz, 1H), 7.93-7.83 (m, 2H), 7.40 (t, J = 7.1 Hz, 1H), 5.76 (s, 2H), 4.74-4.54 (m, 1H), 4.13 (s, 2H), 3.84 (dt, J = 11.7, 6.7 Hz, 1H), 3.58-3.40 (m, 6H), 3.28 (d, J = 12.9 Hz, 3H), 1.56 (d, J = 6.8 Hz, 3H). | Method A using (3S,4S)-1-[(2R)-2-aminopropyl]pyrrolidine-3,4-diol; hydrochloride (152 mg, 0.773 mmol) prepared according Method C and intermediate 1 (40 mg, 0.138 mmol) followed by Method B to give 2.6 mg (0.005 mmol, 16% yield) |

-continued

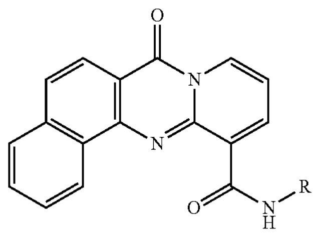

| Ex. | Name | R | Analytical Data | Preparation Information |
|---|---|---|---|---|
| 28 | N-((S)-1-((S)-3-hydroxypyrrolidin-1-yl)propan-2-yl)-7-oxo-7H-benzo[h]pyrido[2,1-b]quinazoline-12-[(2S)-2-aminopropyl] pyrrolidin-3-ol; hydrochloride (165 mg, carboxamide hydrochloride | 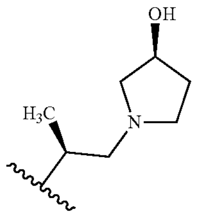 [SMILES: *[C@@H](C)CN1CC[C@H](O)C1] | MS, ES$^+$ m/z, 417 (M + 1) $^1$H NMR (600 MHz, DMSO-$d_6$) δ 10.56 (d, J = 8.4 Hz, 1H), 10.48 (d, J = 8.4 Hz, 1H), 9.98 (s, 1H), 9.88 (s, 1H), 9.19 (ddd, J = 7.0, 5.3, 1.7 Hz, 2H), 8.86.8.80 (m, 2H), 8.63 (ddd, J = 7.5, 5.9, 1.7 Hz, 2H), 8.23 (dd, J = 8.8, 1.9 Hz, 2H), 8.18-8.13 (m, 2H), 7.99 (dd, J = 8.8, 2.3 Hz, 2H), 7.93-7.85 (m, 4H), 7.40 (td, J = 7.1, 5.5 Hz, 2H), 4.72-4.65 (m, 2H), 4.46-4.39 (m, 2H), 3.78 (tt, J = 12.0, 6.2 Hz, 3H), 3.67 (s, 3H), 3.61 (s, 10H), 3.49 (dddt, J = 38.5, 23.3, 11.2, 5.7 Hz, 11H), 3.33 (ddt, J = 15.3, 11.2, 5.3 Hz, 2H), 3.25-3.17 (m, 2H), 2.31-2.22 (m, 1H), 2.05-1.96 (m, 1H), 1.55 (t, J = 7.0 Hz, 6H). | Method A Using (3S)-1-Using (3S)-1-[(2S)-aminopropyl]pyrrolidin-3-ol; hydrochloride (165 mg, 0.913 mmol) prepared according Method C and intermediate 1 (40 mg, 0.138 mmol) followed by Method B to give 6 mg (0.013 mmol, 37% yield) |
| 29 | N-((S)-1-((R)-3-hydroxypyrrolidin-1-yl)propan-2-yl)-7-oxo-7H-benzo[h]pyrido[2,1-b]quinazoline-12-carboxamide hydrochloride | 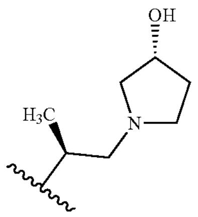 [SMILES: *[C@@H](C)CN1CC[C@@H](O)C1] | MS, ES$^+$ m/z, 417 (M + 1) $^1$H NMR (600 MHz, DMSO-$d_6$) δ 10.60 (d, J = 8.8 Hz, 1H), 10.48 (d, J = 8.6 Hz, 1H), 9.82 (d, J = 31.8 Hz, 2H), 9.23-9.17 (m, 2H), 8.86-8.79 (m, 2H), 8.65 (ddd, J = 10.2, 7.0, 1.7 Hz, 2H), 8.24 (dd, J = 8.8, 2.8 Hz, 2H), 8.18-8.13 (m, 2H), 7.99 (dd, J = 8.8, 3.9 Hz, 2H), 7.89 (dtd, J = 9.3, 7.0, 5.3 Hz, 4H), 7.41 (dt, J = 8.7, 7.1 Hz, 2H), 4.72-4.68 (m, 2H), 4.46 (s, 1H), 4.38 (dd, J = 4.8, 2.4 Hz, 1H), 3.81-3.76 (m, 1H), 3.74-3.53 (m, 7H), 3.45-3.40 (m, 6H), 3.34 (ddd, J = 12.3, 8.0, 4.7 Hz, 2H), 3.25-3.15 (m, 1H), 2.23 (td, J = 13.2, 9.1 Hz, 1H), 2.03-1.97 (m, 1H), 1.97-1.94 (m, 1H), 1.54 (dd, J = 9.0, 6.8 Hz, 6H). | Method A Using (3R)-1-[(2S)-2-aminopropyl]pyrrolidin-3-ol; hydrochloride (165 mg, 0.913 mmol) prepared according Method C and intermediate 1 (40 mg, 0.138 mmol) followed by Method B to give 2.6 mg (0.005 mmol, 48% yield) |
| 30 | N-((R)-1-((S)-3-hydroxypyrrolidin-1-yl)propan-2-yl)-7-oxo-7H-benzo[h]pyrido[2,1-b]quinazoline-12-carboxamide hydrochloride | 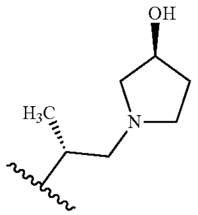 [SMILES: *[C@H](C)CN1CC[C@H](O)C1] | MS, ES$^+$ m/z, 417 (M + 1) $^1$H NMR (600 MHz, DMSO-$d_6$) δ 10.60 (d, J = 8.7 Hz, 1H), 10.47 (d, J = 8.6 Hz, 1H), 9.85 (s, 2H), 9.20 (ddd, J = 9.8, 7.1, 1.7 Hz, 2H), 8.86-8.79 (m, 2H), 8.65 (ddd, J = 9.9, 7.0, 1.7 Hz, 2H), 8.23 (dd, J = 8.8, 3.0 Hz, 2H), 8.18-8.13 (m, 2H), 7.99 (dd, J = 8.8, 4.1 Hz, 2H), 7.89 (dtd, J = 9.0, 7.2, 5.3 Hz, 4H), 7.41 (dt, J = 9.0, 7.1 Hz, 2H), 4.72-4.67 (m, 2H), 4.46 (s, 1H), 4.37 (dt, J = 5.0, 2.5 Hz, 1H), 3.74-3.62 (m, 4H), 3.34 (ddd, J = 12.2, 8.1, 4.7 Hz, 2H), 3.25-3.15 (m, 2H), 2.28-2.19 (m, 1H), 2.03-1.93 (m, 2H), 1.54 (dd, J = 9.2, 6.8 Hz, 6H). | Method A Using (3S)-1-[(2R)-2-aminopropyl]pyrrolidin-3-ol; hydrochloride (165 mg, 0.913 mmol) prepared Method C and intermediate 1 (40 mg, 0.138 mmol) followed by Method B to give 76 mg (0.159 mmol, 98% yield) |
| 31 | N-((R)-1-((R)-3-hydroxypyrrolidin-1-yl)propan-2-yl)-7-oxo-7H-benzo[h]pyrido[2,1-b]quinazoline-12-carboxamide hydrochloride | 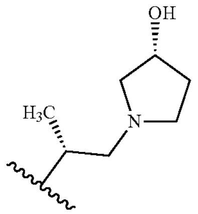 [SMILES: *[C@H](C)CN1CC[C@@H](O)C1] | MS, ES$^+$ m/z, 417 (M + 1) $^1$H NMR (600 MHz, DMSO-$d_6$) δ 10.56 (d, J = 8.5 Hz, 1H), 10.49 (d, J = 8.5 Hz, 1H), 9.95 (s, 1H), 9.81 (s, 1H), 9.19 (ddd, J = 7.1, 4.7, 1.7 Hz, 2H), 8.83 (t, J = 7.3 Hz, 2H), 8.63 (ddd, J = 7.4, 5.9, 1.7 Hz, 2H), 8.23 (dd, J = 8.8, 1.6 Hz, 2H), 8.18-8.13 (m, 2H), 7.99 (dd, J = 8.8, 1.9 Hz, 2H), 7.93-7.85 (m, 4H), 7.40 (td, J = 7.1, 4.9 Hz, 2H), 4.70-4.66 (m, 2H), 4.43-4.39 (m, 1H), 3.78 (tt, J = 12.0, 6.4 Hz, 2H), 3.68-3.63 (m, 1H), 3.22 (ddd, J = 12.2, 7.9, 5.0 Hz, 2H), 2.31-2.22 (m, 1H), 2.05-1.95 (m, 1H), 1.55 (t, J = 6.7 Hz, 6H). | Method A Using (3R)-1-[(2R)-2-aminopropyl]pyrrolidin-3-ol; hydrochloride (165 mg, 0.913 mmol) prepared according Method C and intermediate 1 (50 mg, 0.172 mmol) followed by Method B to give 2.1 mg (0.005 mmol, 32% yield) |
| 32 | N-(2-hydroxyethyl)-7-oxo-7H-benzo[h]pyrido[2,1-b]quinazoline-12-carboxamide; hydrochloride | 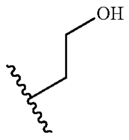 [SMILES: *CCO] | MS, ES$^+$ m/z, 334 (M + 1) $^1$H NMR (600 MHz, DMSO-d6) δ 10.98 (s, 1H), 9.20-9.15 (m, 2H), 8.74 (dd, J = 7.0, 1.7 Hz, 1H), 8.21 (d, J = 8.8 Hz, 1H), 8.11 (d, J = 7.9 Hz, 1H), 7.96 (d, J = 8.7 Hz, 1H), 7.87 (ddd, J = 8.0, 6.9, 1.2 Hz, 1H), 7.80 (ddd, J = 8.2, 7.0, 1.3 Hz, 1H), 7.38 (t, J = 7.1 Hz, 1H), 3.77 (t, J = 5.4 Hz, 3H). | Method A Using 2aminoethan-1-ol (17 mg, 0.280 mmol) and intermediate 1 (40 mg, 0.138 mmol) followed by Method B to give 5.8 mg |

-continued

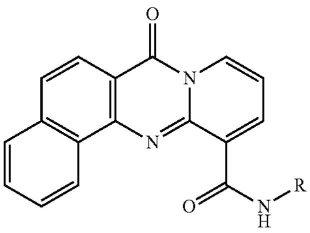

| Ex. | Name | R | Analytical Data | Preparation Information |
|---|---|---|---|---|
| 33 | (S)-N-(2-(3-fluoropyrrolidin-1-yl)ethyl)-7-oxo-7H-benzo[h]pyrido[2,1-b]quinazoline-12-carboxamide; hydrochloride | 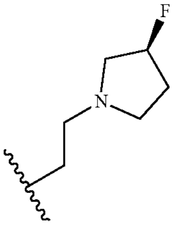 [SMILES: *CCN1CC[C@H](F)C1] | MS, $ES^+$ m/z, 405 (M + 1) $^1H$ NMR (600 MHz, DMSO-d6) δ 10.70 (t, J = 6.0 Hz, 1H), 10.56 (s, 1H), 9.19 (d, J = 7.1 Hz, 1H), 8.86-8.81 (m, 1H), 8.65-8.59 (m, 1H), 8.23 (d, J = 8.8 Hz, 1H), 8.16-8.12 (m, 1H), 7.98 (d, J = = 8.8 Hz, 1H), 7.89 (dd, J = 6.1, 2.9 Hz, 2H), 7.39 (t, J = 7.1 Hz, 1H), 5.48 (dd, J = 53.5, 23.7 Hz, 1H), 4.00 (q, J = = 6.3 Hz, 3H), 3.83 (d, J = 7.9 Hz, 1H), 3.63-3.55 (m, 3H), 2.24-2.06 (m, 1H). | Method A Using (S)-2-(3-fluoropyrrolidin-1-yl)ethan-1-amine hydrochloride (47 mg, 0.280 mmol) prepared according Method C and intermediate 1 (40 mg, 0.138 mmol) followed by Method B to give 5 mg |
| 34 | N-(3-(8-oxa-3-azabicyclo[3.2.1]octan-3-yl)propyl)-7-oxo-7H-benzo[h]pyrido[2,1-b]quinazoline-12-carboxamide; hydrochloride | 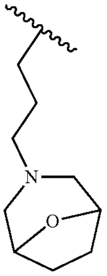 [SMILES: *CCCN1CC2CCC(C1)O2] | MS, $ES^+$ m/z, 443 (M + 1) $^1H$ NMR (500 MHz, DMSO-d6) δ 10.65 (t, J = 6.0 Hz, 1H), 9.83 (s, 1H), 9.18 (dd, J = 7.1, 1.7 Hz, 1H), 8.81 (d, J = 8.1 Hz, 1H), 8.61 (dd, J = 7.0, 1.7 Hz, 1H), 8.23 (d, J = 8.8 Hz, 1H), 8.17-8.12 (m, 1H), 8.01-7.86 (m 3H), 7.38 (t, J = 7.1 Hz, 1H), 4.47 (s, 2H), 3.65 (q, J = 6.8 Hz, 5H), 3.40-3.34 (m, 2H), 3.22 (dt, J = 10.2, 5.2 Hz, 2H), 3.10 (t, J = 9.8 Hz, 2H), 2.22-2.08 (m, 4H), 1.98-1.92 (m, 2H) | Method A Using 3-(8-oxa-3-azabicyclo[3.2.1]octan-3-yl)propan-1-amine (47 mg, 0.280 mmol) and intermediate 1 (40 mg, 0.138 mmol) followed by Method B to give 32.2 mg |
| 35 | (R)-N-(2-(2-methylpyrrolidin-1-yl)ethyl)-7-oxo-7H-benzo[h]pyrido[2,1-b]quinazoline-12-carboxamide; hydrochloride 1 | 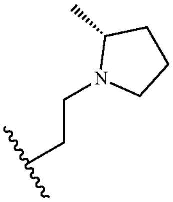 [SMILES: *CCN1CCC[C@H]1C] | MS, $ES^+$ m/z, 401 (M + 1) $^1H$ NMR (500 MHz, DMSO-d6) δ 10.62 (t, J = 5.9 Hz, 2H), 9.79 (s, 1H), 9.19 (dd, J = 7.1, 1.7 Hz, 2H), 8.88-8.83 (m, 2H), 8.60 (dd, J = 7.0. 1.7 H2, 2H), 8.23 (d, J = 8.8 Hz, 2H), 8.17-8.12 (m, 2H), 7.99 (d, J = 8.8 Hz, 2H), 7.90 (dd, J = 6.2, 3.2 Hz, 4H), 7.39 (t, J = 7.1 Hz, 2H), 4.00 (q, J = 6.5 Hz, 6H), 3.58 ~ 3.51 (m, 5H), 3.35 (dd, J = 13.6, 7.2 Hz, 3H), 3.27 (d, J = 8.8 Hz, 2H), 2.20 (dd, J = 12.9, 7.3 Hz, 2H), 2.01-1.88 (m, 4H), 1.67-1.58 (m, 2H), 1.40 (d, J = 6.5 Hz, 6H), 1.26 (d, J = 6.8 Hz, 1H). | Method A Using (R)-2-(2-methylpyrrolidin-1-yl)ethan-1-amine hydrochloride (46 mg, 0.280 mmol) prepared according Method C and intermediate 1 (46 mg, 0.138 mmol) followed by Method B to give 19.6 mg |
| 36 | (S)-N-(2-(2-methylpyrrolidin-1-yl)ethyl)-7-oxo-7H-benzo[h]pyrido[2,1-b]quinazoline-12-yl)ethan-1-carboxamide; hydrochloride | 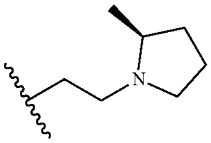 [SMILES: *CCN1CCC[C@@H]1C] | MS, $ES^+$ m/z, 401 (M + 1) $^1H$ NMR (500 MHz, DMSO-d6) δ 10.62 (t, J = 5.8 Hz, 1H), 9.18 (dd, J = 7.2, 1.6 Hz, 1H), 8.89-8.83 (m, 1HD), 8.59 (dd, J = 7.0, 1.6 Hz, 1H), 8.23 (d, J = 8.8 Hz, 1H), 8.14 (dd, J = 6.5, 2.8 Hz, 1H), 7.98 (d, J = 8.8 Hz, 1H), 7.93-7.87 (m, 2H), 7.39 (t, J = 7.1 Hz, 1H), 4.04-3.97 (m, 6H), 3.80-3.72 (m, 5H), 3.56-3.47 (m, 1H), 3.34 (dq, J = 13.3, 6.7 Hz, 1H), 3.28-3.19 (m, 1H), 2.20 (dt, J = 12.4. 5.9 Hz, 1H), 2.00-1.87 (m, 2H), 1.68-1.56 (m, 1H), 1.40 (d, J = 6.4 Hz, 3H) | Method A Using (S)-2-(2-methylpyrrolidin-1-amine hydrochloride (46 mg, 0.280 mmol) prepared according Method C and intermediate 1 (40 mg, 0.138 mmol) followed by Method B to give 17.3 mg |
| 37 | N-((1-methylazetidin-3-yl)methyl)-7-oxo-7H-benzo[h]pyrido[2,1-b]quinazoline-12-carboxamide; hydrochloride | 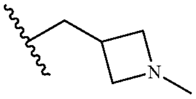 [SMILES: *CC1CN(C)C1] | MS, $ES^+$ m/z, 373 (M + 1) $^1H$ NMR (600 MHz, DMSO-d6) δ 10.56 (t, J = 5.7 Hz, 1H), 9.71 (s, 1H), 9.17 (dd, J = 7.1, 1.7 Hz, 1H), 8.84-8.80 (m, 1H), 8.59 (dt, J = 7.0, 2.1 Hz, 1H), 8.23 (d, J = 8.8 Hz, 1H), 8.16-8.12 (m, 1H), 7.98 (d, J = 8.7 Hz, 1H), 7.95-7.86 (m, 2H), 7.38 (t, J = 7.1 Hz, 1H), 3.73-3.59 (m, 3H), 3.47 (ddq, J = 12.4, 7.0, 3.0 Hz, 1H), 3.11 (ddt, J = 15.8, 12.3, 7.6 Hz, 2H), 2.22-2.12 (m, 3H), 1.93 (dddt, J = 21.5, 12.9, 8.8, 4.9 Hz, 2H), 1.61 (dq, J = 12.9. 9.1 Hz, 1H), 1.35 (d, J = 6.5 Hz, 3H). | Method A Using (1-methylazetidin-3-yl)methanamine dihydrochloride (48 mg, 0.280 mmol) and intermediate 1 (40 mg, 0.138 mmol) followed by Method B to give 28.5 mg |

-continued

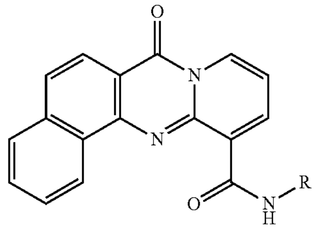

| Ex. | Name | R | Analytical Data | Preparation Information |
|---|---|---|---|---|
| 38 | N-(3-(dimethylamino) propyl)-7-oxo-7H-benzo[h]pyrido[2,1-b]quinazoline-12-carboxamide; hydrochloride | 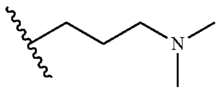 [SMILES: *CCCN(C)C] | MS, $ES^+$ m/z, 375 (M + 1) $^1$H NMR (600 MHz, DMSO-d6) δ 10.58 (t, J = 5.7 Hz, 1H), 9.87 (s, 1H), 9.17 (dd, J = 7.1, 1.6 Hz, 1H), 8.81 (d, J = 7.9 Hz, 1H), 8.60 (dd, J = 7.0, 1.7 Hz, 1H). 8.23 (d, J = 8.8 Hz, 1H), 8.14 (d, J = 8.6 Hz, 1H), 7.98 (d, J = 8.8 Hz, 1H), 7.94-7.86 (m, 2H), 7.38 (t, J = 7.0 Hz, 1H), 3.67 (q, J = 6.9 Hz, 2H), 3.22 (dt, J = 10.6, 5.5 Hz, 2H), 2.79 (d, J = 4.9 Hz, 6H), 2.13 (p, J = 7.3 Hz, 2H). | Method A Using $N^1,N^1$-dimethylpropane-1,3diamine (28 mg, 0.280 mmol) and intermediate 1 (40 mg, 0.138 mmol) followed by Method B to give 34.0 mg |
| 39 | (S)-N-(3-(3-hydroxypyrrolidin-1-yl)propyl)-7-oxo-7H-benzo[h]pyrido[2,1-b]quinazoline-12-carboxamide hydrochloride | 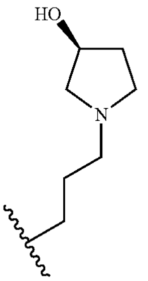 [SMILES: *CCCN1CC[C@H](O)C1] | MS, $ES^+$ m/z, 417 (M + 1) $^1$H NMR (600 MHz, DMSO-26) δ 10.82 (s, 1H), 10.60-10.54 (m, 2H), 10.35 (s, 1HD), 9.15 (ddd, J = 7.1, 4.4, 1.7 H2, 2H). 8.79 (d, J = = 8.1 Hz, 2H), 8.62-8.57 (m, 2H), 8.21 (dd, J = 8.8, 4.3 Hz, 2H), 8.15-8.10 (m, 2H), 7.99-7.85 (m, 6H), 7.37 (td, J = 7.1.3.7 Hz, 2H), 4.45-4.37 (m, 2H), 3.71-3.58 (m, 13H), 3.41 (dd, J = 11.7, 5.1 Hz, 2H), 3.37-3.33 (m, 2H), 3.33-3.26 (m, 3HD), 3.21 (ddd, J = 11.2, 7.2, 4. 1 Hz, 1H), 3.13 (ddd, J = 15.5, 8.6, 4.0 Hz, 2H), 2.95 (d, J = 12.4 Hz, 1H), 2.28-2.11 (m, 5H), 2.03-1.94 (m, 1H), 1.91 (dd, J = 11.9, 7.4 Hz, 1H), 1.87-1.79 (m, 1H). | Method A Using(S)-1-(3-aminopropyl)pyrrolidin-3-ol (40 mg, 0.280 mmol) and intermediate 1 (40 mg, 0.138 mmol) followed by Method B to give 40.9 mg |
| 40 | (R)-N-(3-(3-hydroxypyrrolidin-1-yl)propyl)-7-oxo-7H-benzo[h]pyrido[2,1-b]quinazoline-12-carboxamide; hydrochloride | 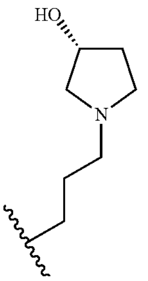 [SMILES: *CCCN1CC[C@@H](O)C1] | MS, $ES^+$ m/z, 417 (M + 1) $^1$H NMR (500 MHz, DMSO-d6) δ 10.78 (s, 1H), 10.57 (q, J = 5.9 Hz, 2H), 10.32 (s, 1HD). 9.16 (ddd, J = 7.1.3.4, 1.7 H2, 2H). 8.79 (d, J = 7.9 Hz, 2H), 8.59 (dt, J = 7.0, 1.8 Hz, 2H), 8.21 (dd, J = 8.8, 3.3 Hz, 2H), 8.16-8.10 (m, 2H), 7.99-7.85 (m, 6H). 7.37 (td, J = 7.1, 2.9 Hz, 2H), 4.45-4.36 (m, 2H), 3.68 (s, 10H), 3.60 (s, 3B), 3.44-3.37 (m, 2H), 3.37-3.31 (m, 2H), 3.29 (dq, J = 8.9, 6.3, 4.5 Hz, 2H), 3.23-3.16 (m, 1H), 3.13 (ddd, J = 12.9, 8.5, 4.8 Hz, 2H), 2.95 (d, J = 12.5 Hz, 1H), 2.19 (ddt, J = 36.0, 12.5, 6.7 Hz, 5H), 2.03-1.95 (m, 1HD), 1.95-1.88 (m, 1H), 1.84 (dt, J = 13.8. 7.4 Hz, 1H). | Method A Using(R)-1-(3-aminopropyl)pyrrolidin-3-ol (40 mg, 0.280 mmol) and intermediate 1 (40 mg, 0.138 mmol) followed by Method B to give 32.2 mg |

Cell culture: A375 cells (CRL-1619, ATCC) were grown in DMEM (GJBCO) supplemented with 1000 fetal bovine serum (GTBCO) in 5% $CO_2$ at 37° C.

Cell treatment and Imaging: 18 hours post-seeding in cell carrier black 384-well plates (PerkinElmer) at 15 000 cells/well, A375 cells were treated for 4 hours with a positive control or test compounds (9 serial semi-log dilutions, top concentration 10 μM). Upon treatment A375 cells were (i) fixed for 15 min at RT with 4% of paraformaldehyde, (ii) permeabilized for 20 min at RT with 0.1-0.5% of NP-40, (iii) incubated with primary antibodies at 4° C.: anti-RPA194 (1:1000-1:1250 dilution, sc-48385, Santa Cruz Biotechnology) and anti-gH2Ax (1:5000 dilution, 81299, Abcam or 1:4000, JBW302, Millipore) (iv) incubated for 1 h at RT with Hoechst (1:5000 dilution, H3570, ThermoFisher) and secondary antibodies: anti-mouse-AlexaFluor488 (1:2000 dilution, A11001, ThermoFisher) and anti-rabbit-AlexaFluor647 (1:2000 dilution, A21443, ThermoFisher) or goat anti-mouse AlexaFluor-594 (1:1000 dilution). Images were acquired on an Operetta CLS High-Content Analysis System (PerkinElmer) (40× objective; 9 fields/well) and processed using the Columbus Image Analysis System (PerkinElmer) or by using Molecular Devices ImageXpress Micro XLS High Content Imager and MetaXpress high-content acquisition and analysis software.

Cell viability assay: 18 hours post-seeding in white 384-Viewplate (6007480, PerkinElmer) at 800 cells/well, or Costar black 96-well plate; (#3603) at 14,000 cells/well, A375 cells were treated for 72 hours with positive controls or test compounds (9 serial semi-log dilutions, top concentration 10 μM). Following treatment, A375 cells were incubated for 10 min at RT with the CellTiter-Glo reagent (G7571, Promega) or CellTiter-Blue® Reagent (G8081, Promega). Measurement of the luminescence signal was performed on an Ensight (PerkinElmer) or Victor Nivo™ Multimode Plate reader.

As the data herein indicate, a broad variety of compounds of Formula (I) were found to effectively destruct RPA194 and inhibit RNA polymerase I (Pol I) at low concentrations. $pIC_{50}$ values for exemplary compounds of Formula (I) are provided in Table B1 below. Any compound with $pIC_{50}$ superior or equal to 5.02 in this assay, as described above, is deemed a Pol I inhibitor. In the table below, (+) is associated with a $pIC_{50}$ 5.02 to 5.8; (++) with $pIC_{50}$ 5.8 to 6.3; and (+++) with a $pIC_{50}$ above 6.3.

TABLE B1

| Example | Compound # | Activity Range |
|---|---|---|
| 1 | 101 | +++ |
| 2 | 105 | +++ |
| 3 | 106 | +++ |
| 4 | 102 | +++ |
| 5 | 103 | +++ |
| 6 | 104 | ++ |
| 7 | 107 | +++ |
| 8 | 108 | + |
| 9 | 109 | ++ |
| 10 | 114 | ++ |
| 11 | 115 | +++ |
| 12 | 116 | ++ |
| 13 | 118 | ++ |
| 14 | 119 | +++ |
| 15 | 120 | ++ |
| 16 | 121 | +++ |
| 17 | 122 | + |
| 18 | 123 | +++ |
| 19 | 130 | ++ |
| 20 | 131 | ++ |
| 21 | 113 | ++ |
| 22 | 110 | ++ |
| 23 | 111 | +++ |
| 24 | 112 | ++ |
| 25 | 117 | + |
| 26 | 124 | ++ |
| 27 | 125 | ++ |
| 28 | 126 | ++ |
| 29 | 127 | ++ |
| 30 | 128 | +++ |
| 31 | 129 | +++ |
| 32 | 132 | + |
| 33 | 133 | + |
| 34 | 134 | + |
| 35 | 135 | + |
| 36 | 136 | + |
| 37 | 138 | + |
| 38 | 139 | + |
| 39 | 140 | + |
| 40 | 137 | + |

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the disclosure (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the disclosure and does not pose a limitation on the scope of the disclosure unless otherwise claimed. No language in the specification should be construed as indicating any non-claimed element as essential to the practice of the disclosure.

Preferred embodiments of this disclosure are described herein, including the best mode known to the inventors for carrying out the disclosure. Variations of those preferred embodiments may become apparent to those of ordinary skill in the art upon reading the foregoing description. The inventors expect skilled artisans to employ such variations as appropriate, and the inventors intend for the disclosure to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

What is claimed is:

1. A compound of Formula (I):

Formula (I)

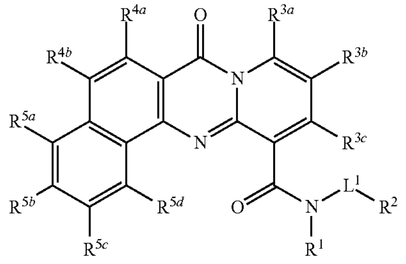

or a pharmaceutically acceptable salt thereof, wherein:

$R^1$ is H or $C_{1-3}$ alkyl;

$R^2$ is selected from the group consisting of:

(a) —$NR^6R^7$, wherein $R^6$ and $R^7$ are independently selected from the group consisting of: H and $C_{1-6}$ alkyl which is optionally substituted with from 1-6 $R^a$;

(b) —$OR^8$, wherein $R^8$ is H or $C_{1-6}$ alkyl which is optionally substituted with from 1-6 $R^a$; and (c) heterocyclyl of 4-12 ring atoms, wherein from 1-3 ring atoms are ring heteroatoms each independently selected from the group consisting of N, NH, $N(R^d)$, O, and $S(O)_{0-2}$, wherein the heterocyclyl is optionally substituted with from 1-6 $R^b$, $L^1$ is a bond or $C_{1-6}$ alkylene which is optionally substituted with from 1-6 $R^c$, provided that when $L^1$ is a bond, then $R^2$ is heterocyclyl that is attached to $L^1$ via a ring carbon atom;

$R^{3a}$, $R^{3b}$, $R^{3c}$, $R^{4a}$, $R^{4b}$, $R^{5a}$, $R^{5b}$, $R^{5c}$, and $R^{5d}$ are each independently selected from the group consisting of: H, halo, $C_{1-6}$ alkyl, $C_{1-6}$ haloalkyl, $C_{1-6}$ alkoxy, $C_{1-6}$ haloalkoxy, and OH;

each occurrence of $R^a$ and $R^c$ is independently selected from the group consisting of: —OH; -halo; —NR'R"; $C_{1-4}$ alkoxy; $C_{1-4}$ haloalkoxy; —C(═O)O($C_{1-4}$ alkyl); —C(═O)($C_{1-4}$ alkyl); —C(═O)OH; —CONR'R"; —$S(O)_{1-2}$NR'R"; —$S(O)_{1-2}$ ($C_{1-4}$ alkyl); and cyano;

each occurrence of $R^b$ is independently selected from the group consisting of: $C_{1-6}$ alkyl; $C_{1-6}$ haloalkyl; oxo; —OH; -halo; —NR'R"; $C_{1-4}$ alkoxy; $C_{1-4}$ haloalkoxy; —C(—O)O($C_{1-4}$ alkyl); —C(═O)($C_{1-4}$ alkyl); —C(═O)OH; —CONR'R"; —$S(O)_{1-2}$NR'R"; —$S(O)_{1-2}$ ($C_{1-4}$ alkyl); and cyano;

each occurrence of $R^d$ is independently $C_{1-6}$ alkyl; —C(O)($C_{1-4}$ alkyl); or —C(O)O($C_{1-4}$ alkyl); and each occurrence of R' and R" is independently H or $C_{1-3}$ alkyl.

2. The compound of claim 1, wherein $L^1$ is $C_{1-6}$ alkylene optionally substituted with from 1-6 $R^c$.

3. The compound of claim 1, wherein $L^1$ is unsubstituted $C_{1-4}$ alkylene.

4. The compound of claim 3, wherein $L^1$ is selected from the group consisting of

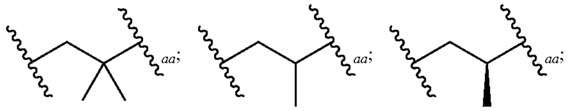

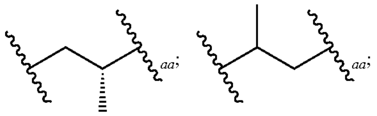

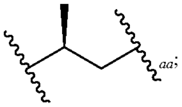 and 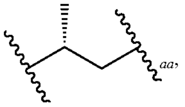

wherein aa is the point of attachment to $R^2$.

5. The compound of claim 1, wherein $R^2$ is $NR^6R^7$.

6. The compound of claim 1, wherein $R^2$ is selected from the group consisting of: $NH(C_{1-3}$ alkyl) and $N(C_{1-3}$ alkyl$)_2$.

7. The compound of claim 6, wherein $R^2$ is $NMe_2$.

8. The compound of claim 1, wherein $R^2$ is heterocyclyl of 4-12 ring atoms, wherein from 1-3 ring atoms are ring heteroatoms each independently selected from the group consisting of N, NH, $N(R^d)$, O, and $S(O)_{0-2}$, wherein the heterocyclyl is optionally substituted with from 1-6 $R^b$.

9. The compound of claim 1, wherein $R^2$ is heterocyclyl of 4-8 ring atoms, wherein from 1-2 ring atoms are ring heteroatoms each independently selected from the group consisting of N, NH, $N(R^d)$, O, and $S(O)_{0-2}$, wherein the heterocyclyl is optionally substituted with from 1-6 $R^b$, wherein at least 1 ring atom is N, NH, or $N(R^d)$.

10. The compound of claim 1, wherein $R^2$ is selected from the group consisting of azetidinyl, pyrrolidinyl, piperidinyl, or 8-oxa-3-azabicyclo[3.2.1]octanyl, each of which is optionally substituted with from 1-2 $R^b$.

11. The compound of claim 1, wherein $R^2$ is pyrrolidinyl which is optionally substituted with from 1-2 $R^b$, wherein the ring nitrogen is optionally substituted with $R^d$.

12. The compound of claim 8, wherein each $R^b$ is independently selected from the group consisting of: halo; —OH; oxo; $C_{1-3}$ alkyl; and $C_{1-3}$ alkoxy.

13. The compound of claim 1, wherein $R^1$ is H.

14. The compound of claim 1, wherein $R^{3a}$, $R^{3b}$, $R^{3c}$, $R^{4a}$, $R^{4b}$, $R^{5a}$, $R^{5b}$, $R^{5c}$, and $R^{5d}$ are each H.

15. The compound of claim 1, wherein the compound is selected from the group consisting of the compounds in the table below, or a pharmaceutically acceptable salt thereof:

| Compound No. | Structure |
|---|---|
| 101 | 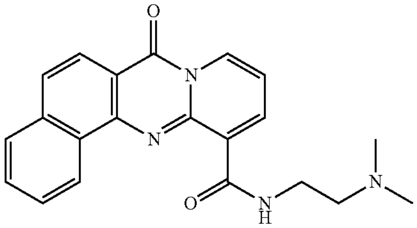 [SMILES: CN(C)CCNC(=O)c1cccn2c(=O)c3ccc4ccccc4c3nc12] |

-continued

| Compound No. | Structure |
|---|---|
| 102 | 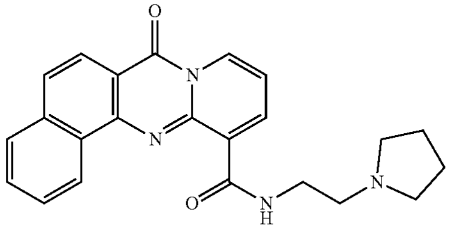 [SMILES: O=C(NCCN1CCCC1)c1cccn2c(=O)c3ccc4ccccc4c3nc12] |
| 103 | 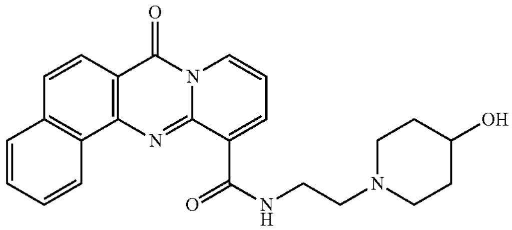 [SMILES: O=C(NCCN1CCC(O)CC1)c1cccn2c(=O)c3ccc4ccccc4c3nc12] |
| 104 | 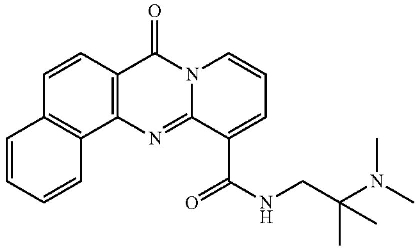 [SMILES: CN(C)C(C)(C)CNC(=O)c1cccn2c(=O)c3ccc4ccccc4c3nc12] |
| 105 | 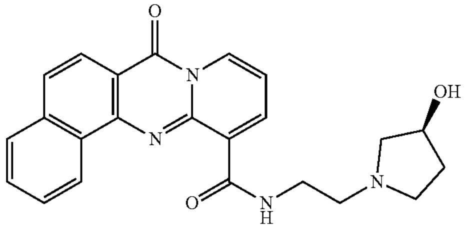 [SMILES: O=C(NCCN1CC[C@H](O)C1)c1cccn2c(=O)c3ccc4ccccc4c3nc12] |
| 106 | 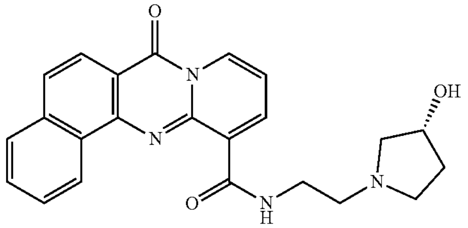 [SMILES: O=C(NCCN1CC[C@@H](O)C1)c1cccn2c(=O)c3ccc4ccccc4c3nc12] |
| 107 | 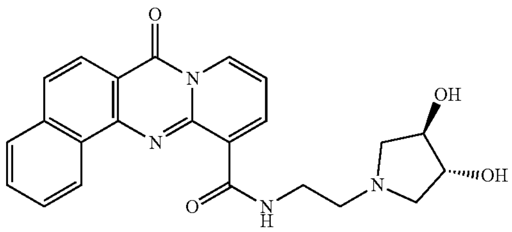 [SMILES: O=C(NCCN1C[C@@H](O)[C@H](O)C1)c1cccn2c(=O)c3ccc4ccccc4c3nc12] |

-continued
| Compound No. | Structure |
|---|---|
| 108 | 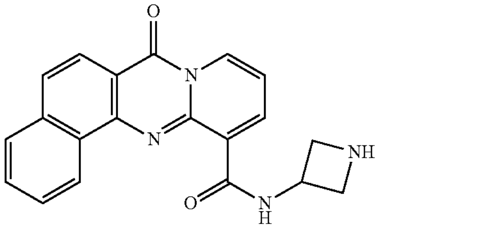 [SMILES: O=C(NC1CNC1)c1cccn2c(=O)c3ccc4ccccc4c3nc12] |
| 109 | 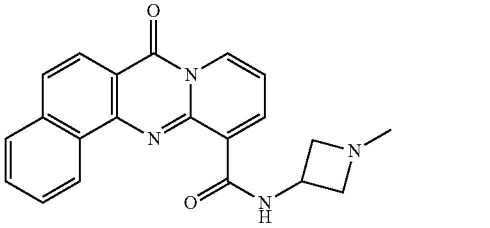 [SMILES: CN1CC(NC(=O)c2cccn3c(=O)c4ccc5ccccc5c4nc23)C1] |
| 110 | 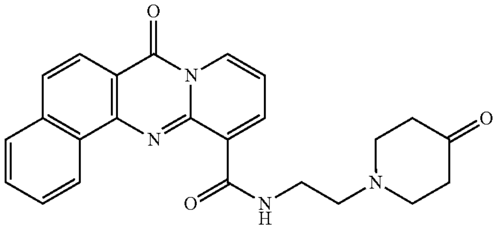 [SMILES: O=C1CCN(CCNC(=O)c2cccn3c(=O)c4ccc5ccccc5c4nc23)CC1] |
| 111 | 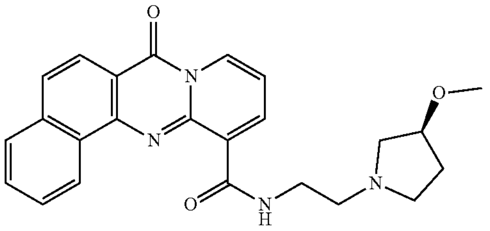 [SMILES: CO[C@H]1CCN(CCNC(=O)c2cccn3c(=O)c4ccc5ccccc5c4nc23)C1] |
| 112 | 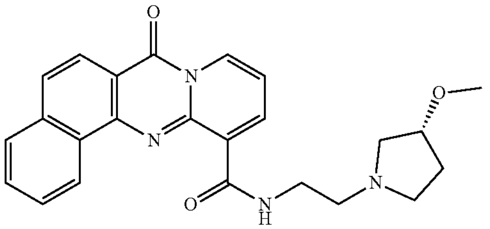 [SMILES: CO[C@@H]1CCN(CCNC(=O)c2cccn3c(=O)c4ccc5ccccc5c4nc23)C1] |
| 113 | 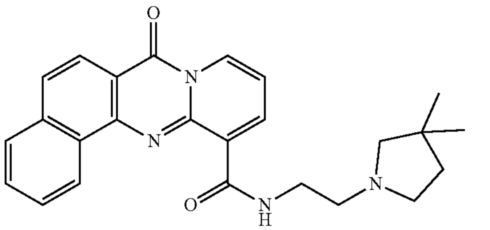 [SMILES: CC1(C)CCN(CCNC(=O)c2cccn3c(=O)c4ccc5ccccc5c4nc23)C1] |
-continued
| Compound No. | Structure |
|---|---|
| 114 | 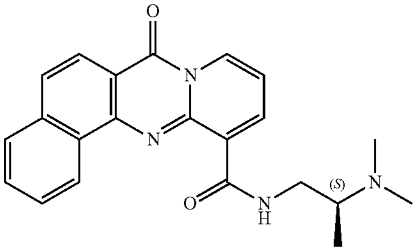 |
| 115 | 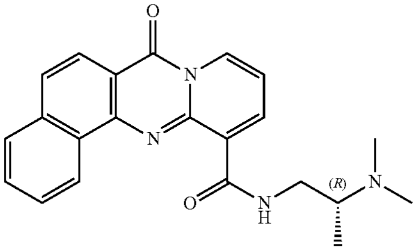 |
| 116 | 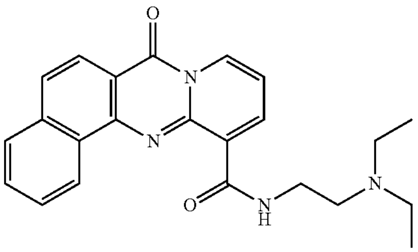 [SMILES: CCN(CC)CCNC(=O)c1cccn2c(=O)c3ccc4ccccc4c3nc12] |
| 117 | 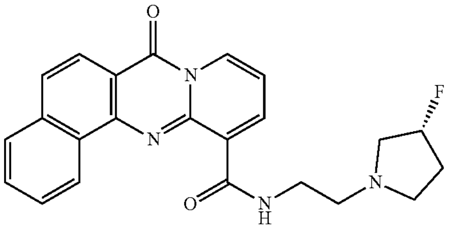 [SMILES: O=C(NCCN1CC[C@@H](F)C1)c1cccn2c(=O)c3ccc4ccccc4c3nc12] |
| 118 | 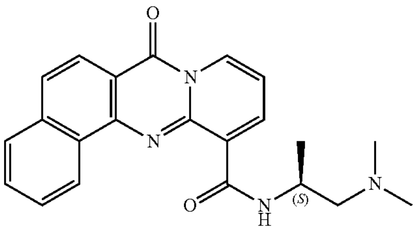 |
| 119 | 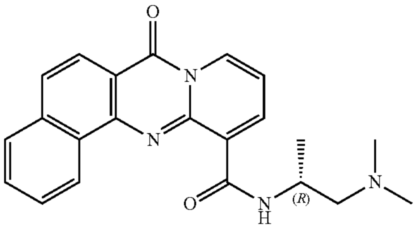 |

-continued
| Compound No. | Structure |
|---|---|
| 120 | 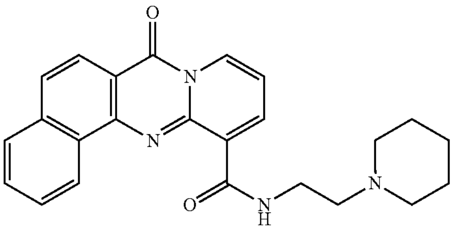 [SMILES: O=C(NCCN1CCCCC1)c1cccn2c(=O)c3ccc4ccccc4c3nc12] |
| 121 | 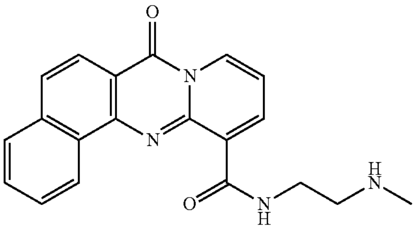 |
| 122 | 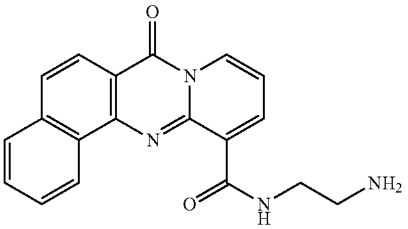 [SMILES: NCCNC(=O)c1cccn2c(=O)c3ccc4ccccc4c3nc12] |
| 123 | 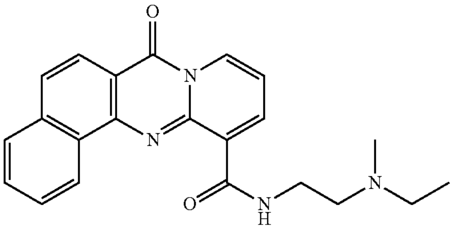 [SMILES: CCN(C)CCNC(=O)c1cccn2c(=O)c3ccc4ccccc4c3nc12] |
| 124 | 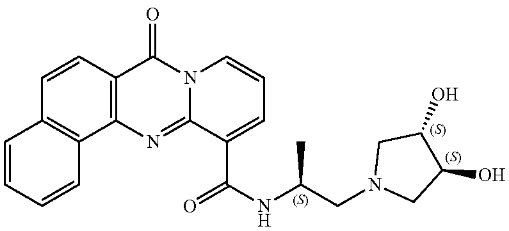 |
| 125 | 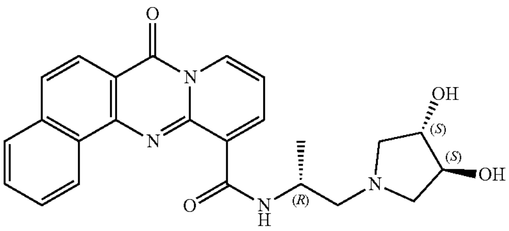 |
-continued
| Compound No. | Structure |
|---|---|
| 126 | 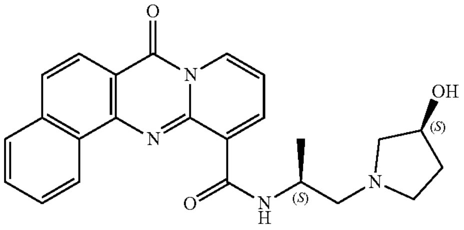 |
| 127 | 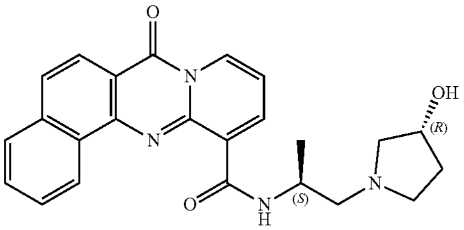 |
| 128 | 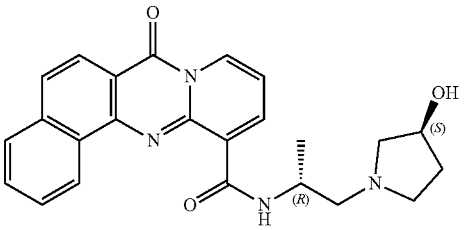 |
| 129 | 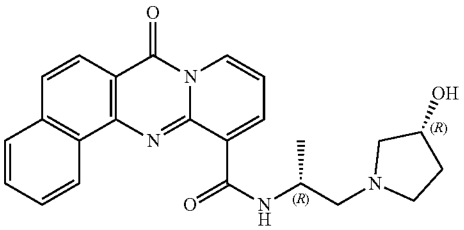 |
| 130 | 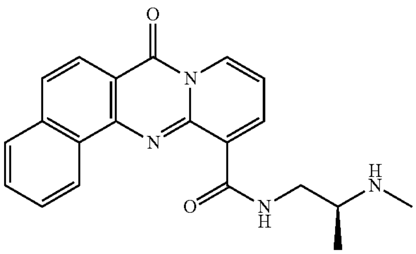 [SMILES: CN[C@@H](C)CNC(=O)c1cccn2c(=O)c3ccc4ccccc4c3nc12] |
| 131 | 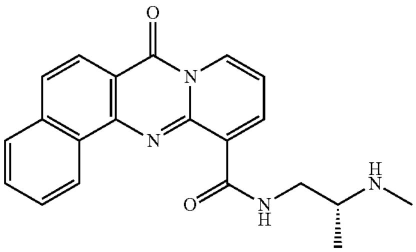 [SMILES: CN[C@H](C)CNC(=O)c1cccn2c(=O)c3ccc4ccccc4c3nc12] |

-continued

| Compound No. | Structure |
| --- | --- |
| 132 | 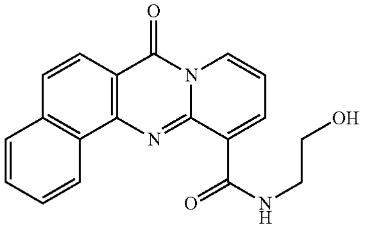 [SMILES: O=C(NCCO)c1cccn2c(=O)c3ccc4ccccc4c3nc12] |
| 133 | 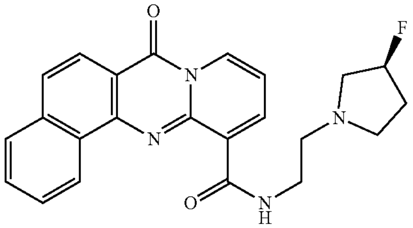 [SMILES: O=C(NCCN1CC[C@H](F)C1)c1cccn2c(=O)c3ccc4ccccc4c3nc12] |
| 134 | 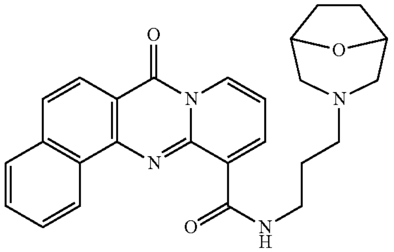 [SMILES: O=C(NCCCN1CC2CCC(C1)O2)c1cccn2c(=O)c3ccc4ccccc4c3nc12] |
| 135 | 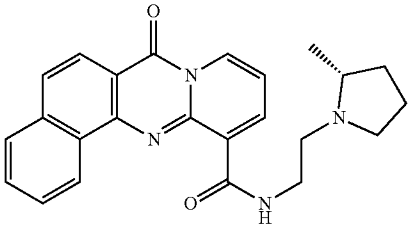 [SMILES: C[C@@H]1CCCN1CCNC(=O)c1cccn2c(=O)c3ccc4ccccc4c3nc12] |
| 136 | 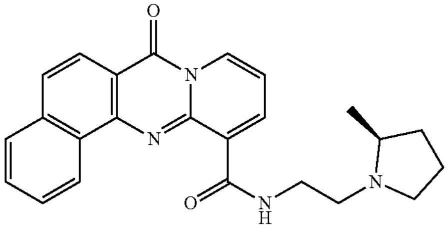 [SMILES: C[C@H]1CCCN1CCNC(=O)c1cccn2c(=O)c3ccc4ccccc4c3nc12] |
| 137 | 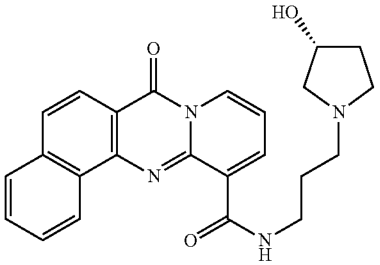 [SMILES: O=C(NCCCN1CC[C@@H](O)C1)c1cccn2c(=O)c3ccc4ccccc4c3nc12] |
| 138 | 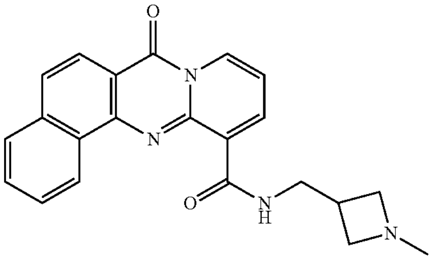 [SMILES: CN1CC(CNC(=O)c2cccn3c(=O)c4ccc5ccccc5c4nc23)C1] |
| 139 | 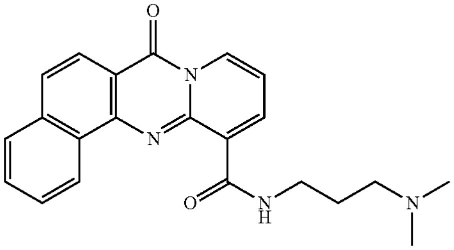 [SMILES: CN(C)CCCNC(=O)c1cccn2c(=O)c3ccc4ccccc4c3nc12] |
| 140 | 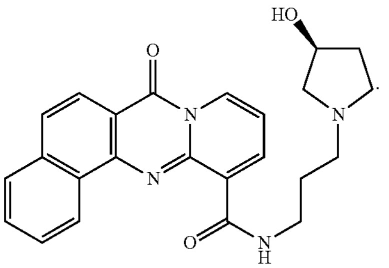 [SMILES: O=C(NCCCN1CC[C@H](O)C1)c1cccn2c(=O)c3ccc4ccccc4c3nc12] |

16. A pharmaceutical composition comprising a compound of claim 1, and a pharmaceutically acceptable carrier.

17. A method for activating upstream p53 pathways in a mammalian cell, wherein the method comprises contacting a cell or population of cells with a compound as claimed in claim 1, or a pharmaceutically acceptable salt thereof.

18. A method for modulating RNA Pol I activity in a mammalian cell, wherein the method comprises contacting a cell or population of cells with a compound as claimed in claim 1, or a pharmaceutically acceptable salt thereof.

19. A method for treating cancer in a subject, wherein the method comprises administering to the subject a compound as claimed in claim 1, or a pharmaceutically acceptable salt thereof.

20. A method for treating an autoimmune disease or disorder in a subject, wherein the method comprises administering to the subject a compound as claimed in claim 1, or a pharmaceutically acceptable salt thereof.

21. A method for treating a condition associated with inflammation or pain in a subject, wherein the method comprises administering to the subject a compound as claimed in claim 1, or a pharmaceutically acceptable salt thereof.

* * * * *